(12) United States Patent
Baker et al.

(10) Patent No.: US 11,150,014 B2
(45) Date of Patent: Oct. 19, 2021

(54) INSULATED CHAMBER WITH PACKETIZED PHASE CHANGE MATERIAL

(71) Applicant: CARON PRODUCTS AND SERVICES, INC., Marietta, OH (US)

(72) Inventors: Milton F. Baker, Vincent, OH (US); Dale C. Barnett, Marietta, OH (US); Robert W. Dotterer, Sardis, OH (US); David N. Figel, Caldwell, OH (US); Stephen C. Keiser, Vienna, WV (US)

(73) Assignee: CARON PRODUCTS AND SERVICES, INC., Marietta, OH (US)

( * ) Notice: Subject to any disclaimer, the term of this patent is extended or adjusted under 35 U.S.C. 154(b) by 572 days.

(21) Appl. No.: 15/936,049

(22) Filed: Mar. 26, 2018

(65) Prior Publication Data
US 2018/0252466 A1 Sep. 6, 2018

Related U.S. Application Data

(63) Continuation-in-part of application No. 14/641,607, filed on Mar. 9, 2015, now Pat. No. 9,927,169, which
(Continued)

(51) Int. Cl.
*F25D 31/00* (2006.01)
*C12M 1/00* (2006.01)
(Continued)

(52) U.S. Cl.
CPC ............. *F25D 31/00* (2013.01); *B01L 1/025* (2013.01); *B01L 7/52* (2013.01); *C12M 41/14* (2013.01);
(Continued)

(58) Field of Classification Search
CPC ......... F25D 2303/082; F25D 2303/085; F25D 2303/0843; F25D 2303/0845;
(Continued)

(56) References Cited

U.S. PATENT DOCUMENTS 3,176,118 A * 3/1965 Scott ...................... F24C 7/087
219/394
4,259,401 A * 3/1981 Chahroudi .............. E04C 1/392
126/618
(Continued)

FOREIGN PATENT DOCUMENTS

CA 2838671 1/2012
DE 102004035017 2/2006
(Continued)

*Primary Examiner* — Jianying C Atkisson
*Assistant Examiner* — Meraj A Shaikh
(74) *Attorney, Agent, or Firm* — John L. DeAngelis; Wolter, Van Dyke, Davis, PLLC

(57) ABSTRACT

An insulated chamber having an interior region for storing items therein includes a phase change material to facilitate controlling the temperature of the interior region and the items. A heating device or cooling device may be used to melt or freeze the phase change material. The phase change material (PCM) may be in various locations such as the walls of the chamber in the form of packets or in the form of containers that serve as shelves and may be removable from the interior region. The packets may have recesses for receiving the items. The phase change material may be within capsules that may be within a liquid or a solid matrix. Controls may be provided to control humidity, oxygen, and carbon dioxide within the interior chamber.

25 Claims, 18 Drawing Sheets

Related U.S. Application Data is a continuation of application No. 12/941,111, filed on Nov. 8, 2010, now abandoned.

(60) Provisional application No. 61/359,143, filed on Jun. 28, 2010.

(51) Int. Cl.
| | |
|---|---|
| *B01L 1/02* | (2006.01) |
| *F24F 5/00* | (2006.01) |
| *B01L 7/00* | (2006.01) |
| *F25D 11/00* | (2006.01) |

(52) U.S. Cl.
CPC .......... *F24F 5/0021* (2013.01); *F25D 11/006* (2013.01); *B01L 2300/043* (2013.01); *B01L 2300/10* (2013.01); *B01L 2300/185* (2013.01); *B01L 2300/1805* (2013.01); *B01L 2300/1844* (2013.01); *B01L 2300/1855* (2013.01); *B01L 2300/1883* (2013.01); *B01L 2300/1894* (2013.01); *Y02E 60/14* (2013.01)

(58) Field of Classification Search
CPC ........ F25D 2331/804; F25D 3/06; F25D 3/08; C12M 41/16; C12M 41/20; C12M 41/18; C12M 41/14; F24F 5/0021
USPC ......... 62/315, 316, 338, 371, 372, 440, 466; 236/3, 4, 44 A; 220/592.01, 592.26
See application file for complete search history.

(56) References Cited

U.S. PATENT DOCUMENTS

| | | | |
|---|---|---|---|
| 4,701,415 A * | 10/1987 | Dutton | C12M 41/14 435/286.6 |
| 4,936,377 A | 6/1990 | Devogel | |
| 4,951,481 A | 8/1990 | Negishi | |
| 5,647,226 A | 7/1997 | Scaringe | |
| 5,899,088 A | 5/1999 | Purdum | |
| 5,950,450 A | 9/1999 | Meyer | |
| 6,308,518 B1 * | 10/2001 | Hunter | F25B 21/02 62/3.3 |
| 6,412,545 B1 * | 7/2002 | Buff | F28D 20/02 165/10 |
| 6,822,198 B2 * | 11/2004 | Rix | A61J 1/165 165/64 |
| 7,422,143 B2 | 9/2008 | Mayer | |
| 7,516,600 B1 | 4/2009 | Flora | |
| 7,913,511 B2 | 3/2011 | Meyer | |
| 8,651,391 B2 | 2/2014 | Patch | |
| 8,904,810 B2 * | 12/2014 | Schabron | F25D 3/08 62/60 |
| 2005/0227037 A1 * | 10/2005 | Booska | C09K 5/063 428/68 |
| 2005/0279730 A1 * | 12/2005 | Miyake | B01L 3/5085 216/41 |
| 2008/0197139 A1 * | 8/2008 | Goncharko | F25D 3/06 220/592.25 |
| 2008/0302127 A1 * | 12/2008 | Cote | F25D 31/006 62/457.7 |
| 2009/0019864 A1 * | 1/2009 | Bruce | F25D 3/14 62/60 |
| 2009/0038557 A1 | 2/2009 | Meter | |
| 2009/0227008 A1 * | 9/2009 | Busujima | C12M 41/48 435/289.1 |
| 2009/0305397 A1 * | 12/2009 | Dodgson | C12M 23/12 435/305.3 |
| 2010/0024439 A1 | 2/2010 | Finke | |
| 2010/0170286 A1 * | 7/2010 | Ghiraldi | F25D 11/006 62/434 |
| 2011/0277489 A1 * | 11/2011 | Schalla | F25D 3/06 62/89 |
| 2012/0072046 A1 * | 3/2012 | Tattam | B65D 90/023 700/300 |

FOREIGN PATENT DOCUMENTS

| | | |
|---|---|---|
| DE | 202006010757 | 12/2006 |
| EP | 1901054 | 3/2008 |
| EP | 2000529 | 10/2008 |
| GB | 1338553 | 11/1973 |
| WO | WO9519533 | 7/1995 |
| WO | WO2006008276 | 1/2006 |
| WO | WO2006010757 | 2/2006 |

* cited by examiner

INSULATED CHAMBER WITH PACKETIZED PHASE CHANGE MATERIAL

CROSS REFERENCE TO RELATED APPLICATIONS

This application is a continuation-in-part application claiming priority from the patent application filed on Mar. 9, 2015, assigned application Ser. No. 14/641,607, and entitled Insulated Chamber with Phase Change Material, now U.S. Pat. No. 9,927,169, which is a continuation application claiming priority from the patent application filed on Nov. 8, 2010, assigned application Ser. No. 12/941,111, and entitled Insulated Chamber with Phase Change Material, which claims priority from U.S. Provisional Application No. 61/359,143 filed Jun. 28, 2010; the disclosure of each of these applications are incorporated herein by reference.

BACKGROUND OF THE INVENTION

Technical Field

The present invention relates generally to insulated chambers such as incubators, environmental chambers, freezers, refrigerators and ovens. More particularly, the present invention relates to an insulated chamber in which a phase change material enhances temperature control.

Background Information

Insulated chambers may be used for a variety of purposes. For instance, such chambers may include incubators, environmental chambers, freezers, refrigerators and ovens. Incubators are typically used for growing cultures in a controlled environment, wherein temperature, humidity, and atmospheric gas concentration are maintained at selected levels. For certain applications it is highly desirable to have both temperature and gas concentrations maintained within strict tolerances while still allowing easy access to the incubator chamber for adding or removing items to and from the chamber or for inspecting the contents of the chamber. Control of environmental variables is desirable to maintain accuracy and reproducibility of incubation results. Typical incubators have used either open-coil heaters within the incubator chamber or water jackets surrounding the incubator chamber. However, while such configurations can be effective in heating an incubator, they do not necessarily provide as strict a control on the incubator temperature as is desirable for consistent results.

Conventional air heater type incubators lack the temperature stability of the water jacket type. Water-jacketed incubators maintain temperature by surrounding the interior chamber with heated water in a separate compartment. The water is heated and circulates around the inner chamber via natural convection. The heat from the water radiates to the interior chamber to maintain a substantially constant temperature inside. Water is an effective thermal insulator and the water-jacket system is considered a more reliable method of heating in case of a power outage. In the wake of a power failure, a water-jacketed incubator will hold a set temperature inside the chamber 4-5 times longer than a radiant-walled unit.

Radiant-walled incubators heat the interior chamber using heaters mounted in the surrounding cavity that radiate heat through to the inside chamber. A radiant-walled heating system allows for quick recovery of temperature following door openings or changes in temperature settings. Radiant-walled heating systems are also more simplified for the user, not requiring filling, monitoring, and emptying water in the water jacket.

A fan may be mounted outside of the culturing area to help to circulate the air inside the chamber without disturbing cultures. This gentle circulation helps maintain a consistent temperature throughout the chamber and speeds recovery of internal temperature as well as $CO_2$ and humidity levels following door openings.

BRIEF SUMMARY OF THE INVENTION

The present invention provides an apparatus comprising: a container defining a storage interior chamber adapted to receive therein a storage item; a first phase change material adjacent the interior chamber and having a first melting or freezing phase change temperature; and a temperature-altering device adjacent the first phase change material and capable of causing the first phase change material to reach the first melting or freezing phase change temperature.

BRIEF DESCRIPTION OF THE SEVERAL VIEWS OF THE DRAWINGS

A preferred embodiment of the invention, illustrated of the best mode in which Applicant contemplates applying the principles, is set forth in the following description and is shown in the drawings and is particularly and distinctly pointed out and set forth in the appended claims.

DETAILED DESCRIPTION OF THE INVENTION

Generally, an incubation chamber (also referred to as an incubator) is used to maintain the chamber contents (also referred to as a product or specimen) at a specified temperature (and other atmospheric conditions). It is preferable to locate the PCM inside chamber walls or within PCM containers that are strategically positioned relative to the product to realize optimal benefits of the PCM. Dependent on the application, PCM may be selected to heat or cool the chamber interior when power is not available to maintain the interior temperature.

Figure 1:
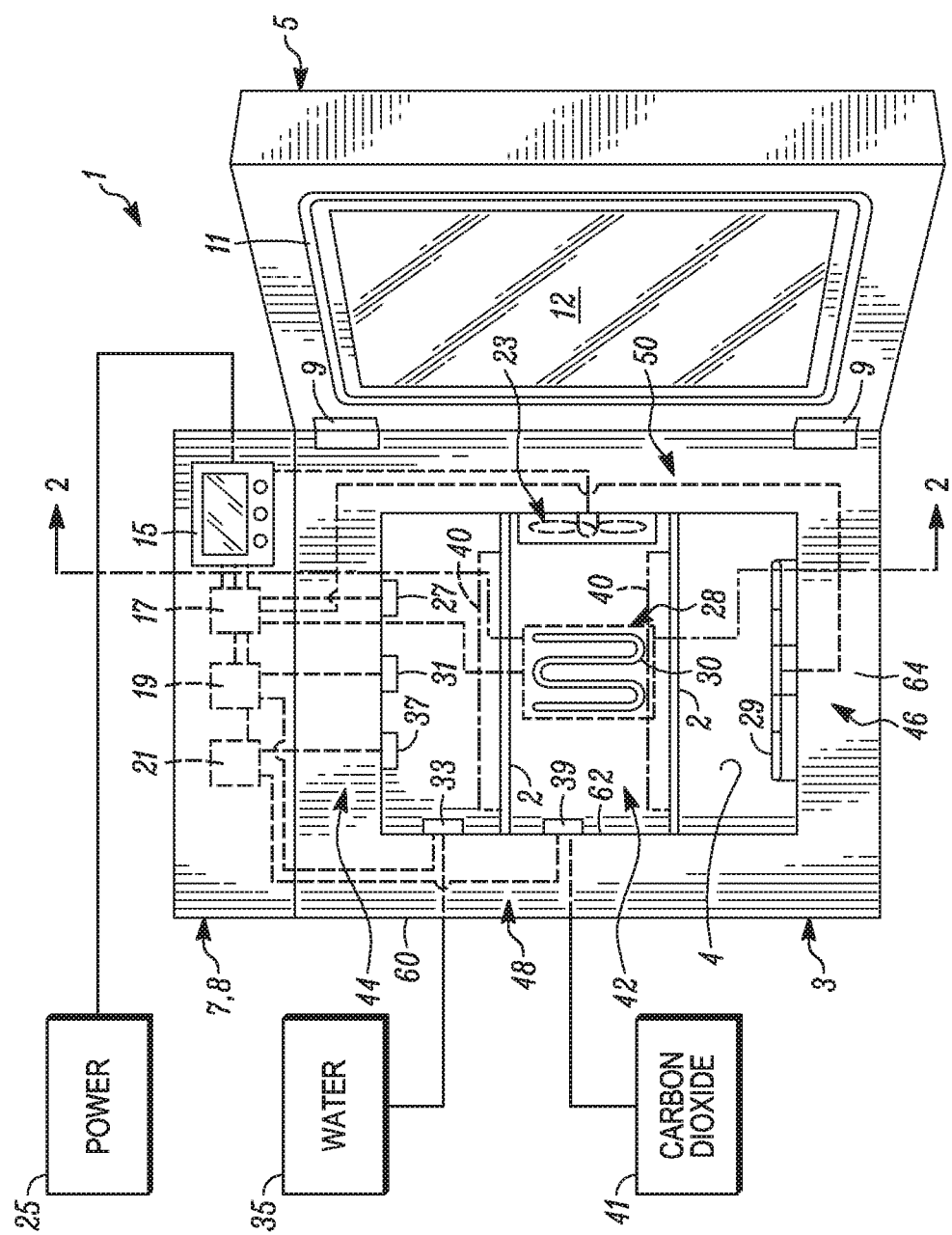
FIG. 1 is a front elevational view of a first embodiment of the insulated chamber of the present invention with portions shown diagrammatically.
Figure 4:
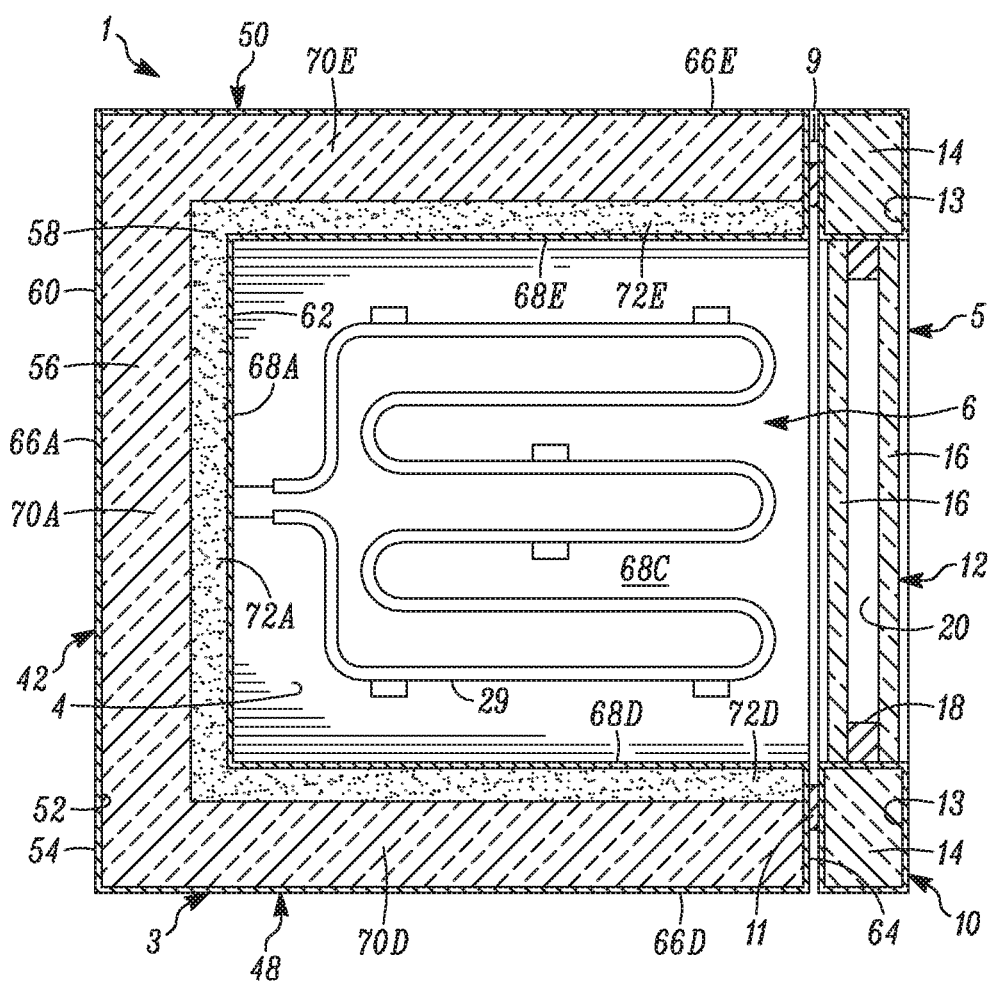
FIG. 4 is a sectional view taken on Line 4-4 of FIG. 2.
Figure 5:
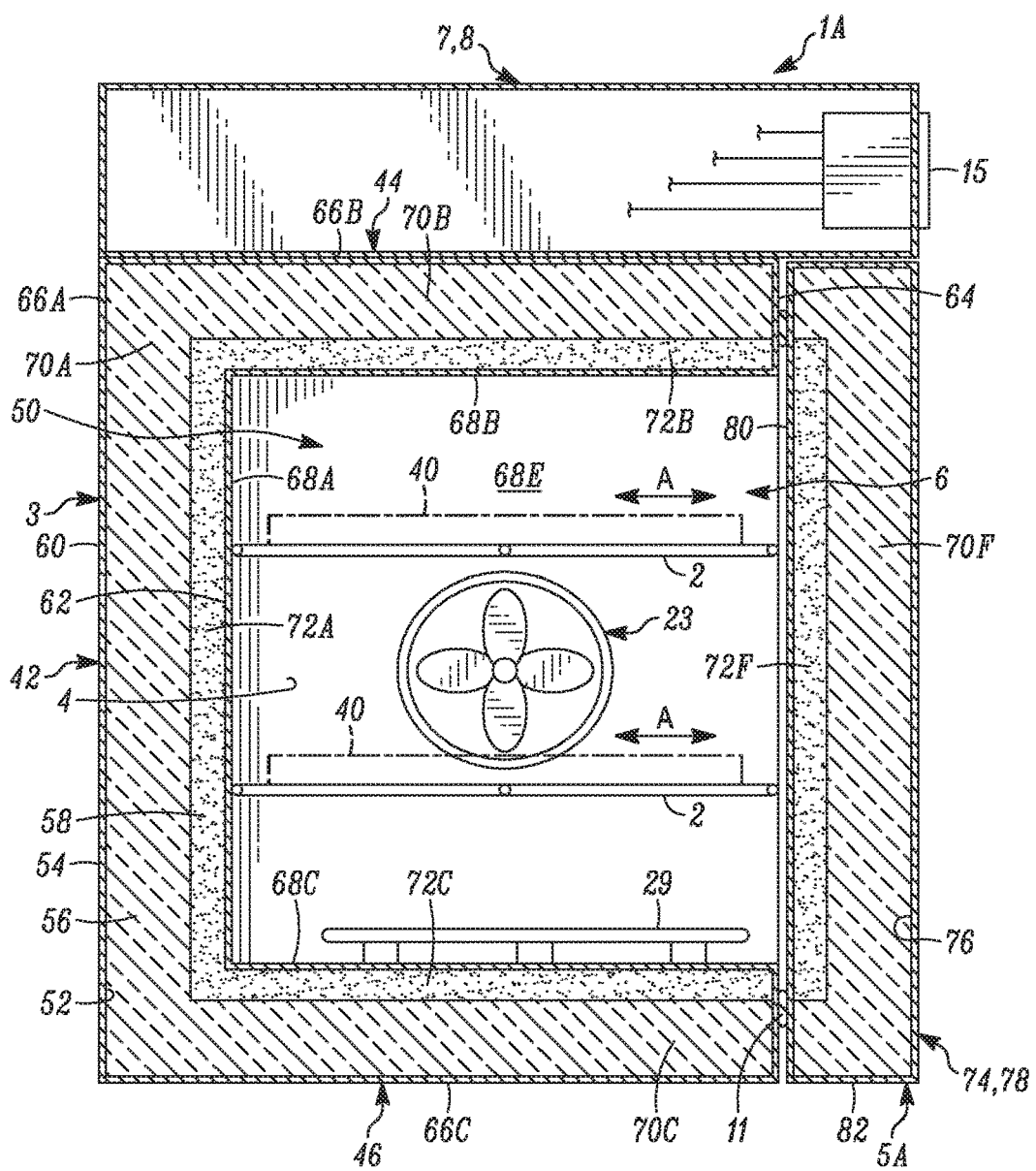
FIG. 5 is similar to FIG. 2 and is a sectional view of a second embodiment of the chamber of the present invention.
Figure 7:
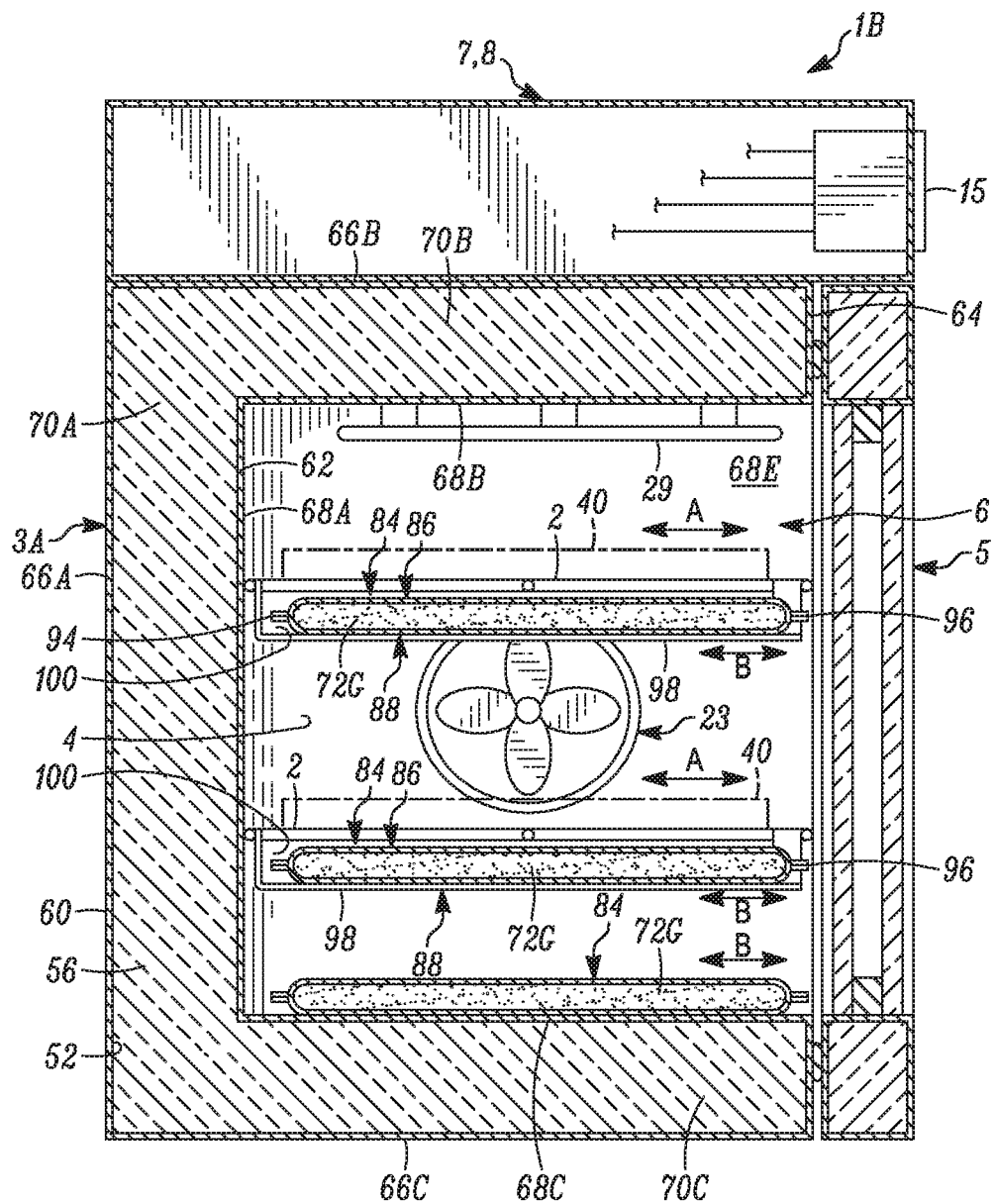
FIG. 7 is a sectional view similar to FIG. 2 of a third embodiment of the chamber of the present invention utilizing the phase change material packets.
Figure 8:
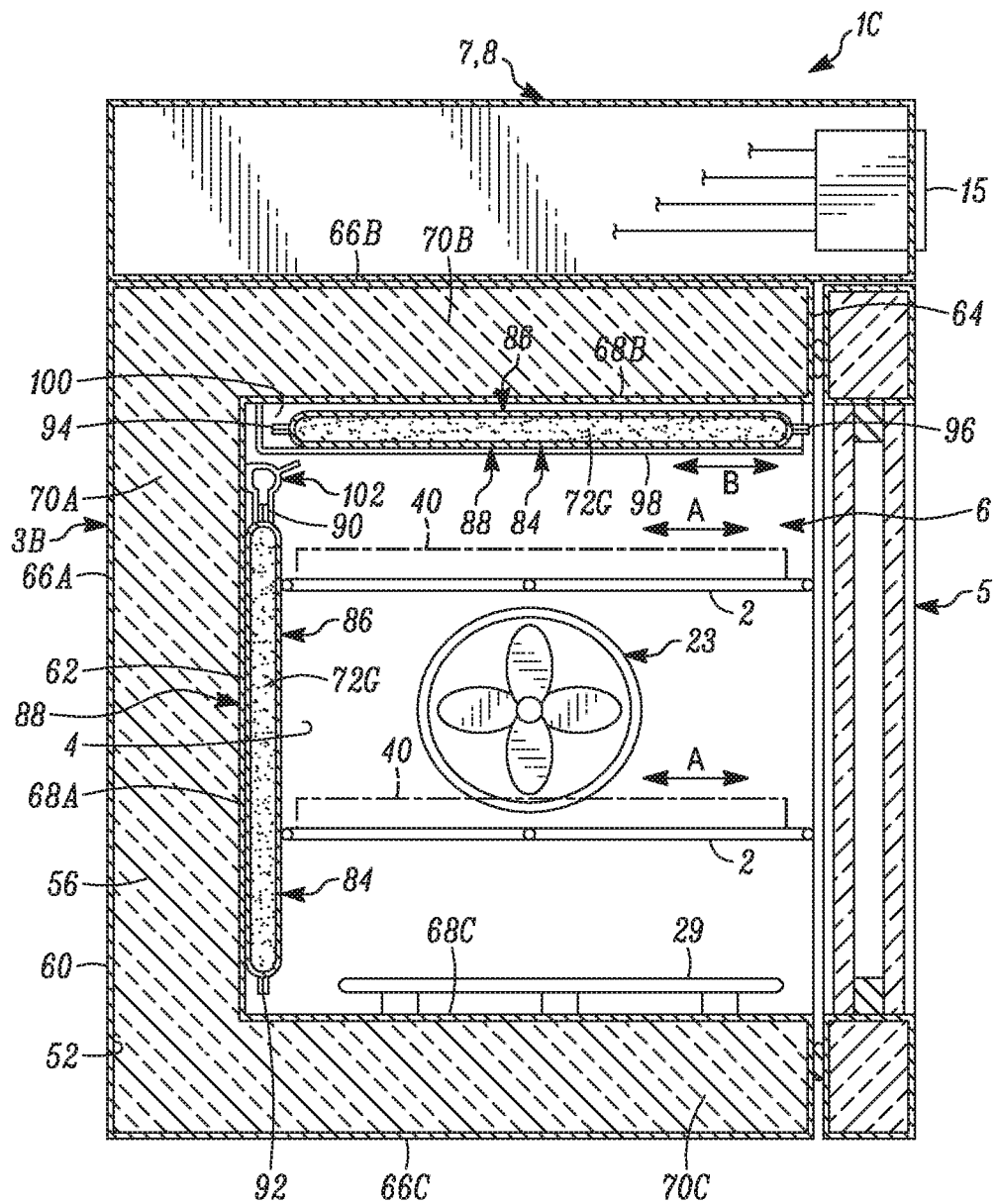
FIG. 8 is a sectional view similar to FIG. 7 of a fourth embodiment of the present invention also utilizing the phase change packets.
Figure 9:
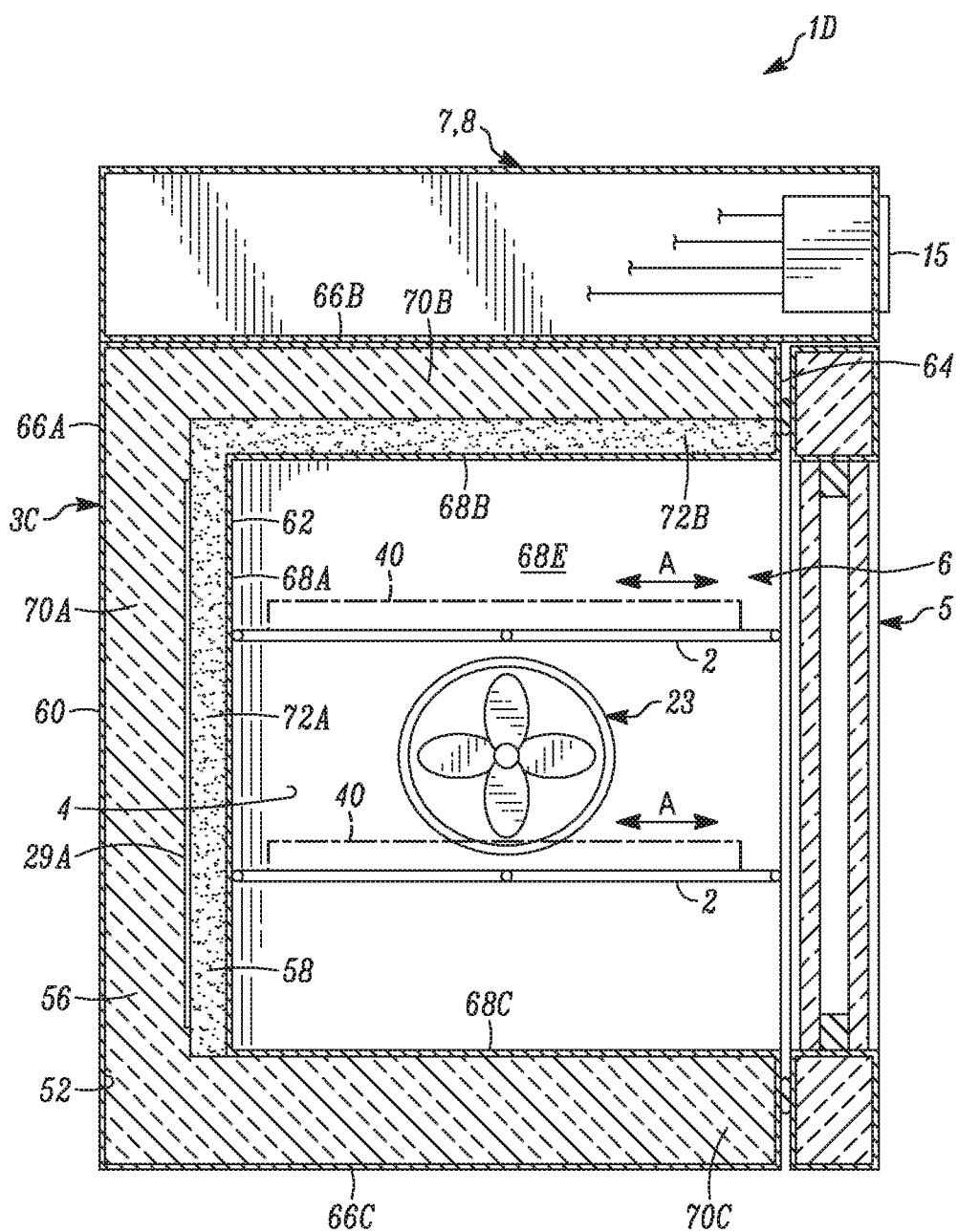
FIG. 9 is a sectional view similar to FIG. 2 of a fifth embodiment of the chamber of the present invention utilizing a heating element between the insulation and phase change material.
Figure 10:
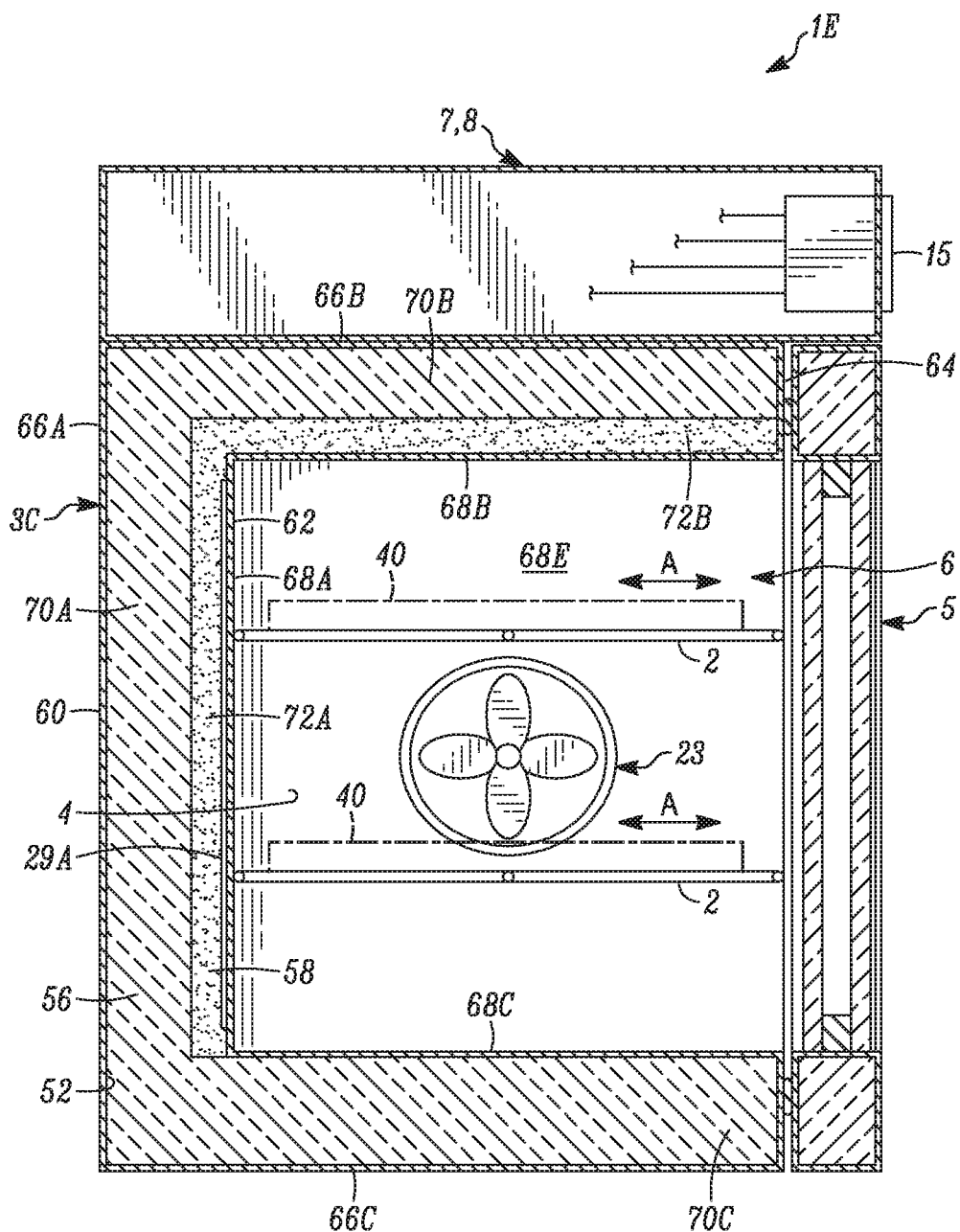
FIG. 10 is a sectional view similar to FIG. 9 of a sixth embodiment of the chamber of the present invention utilizing a heating element between the phase change material and the inner layer of the skin.
Figure 11:
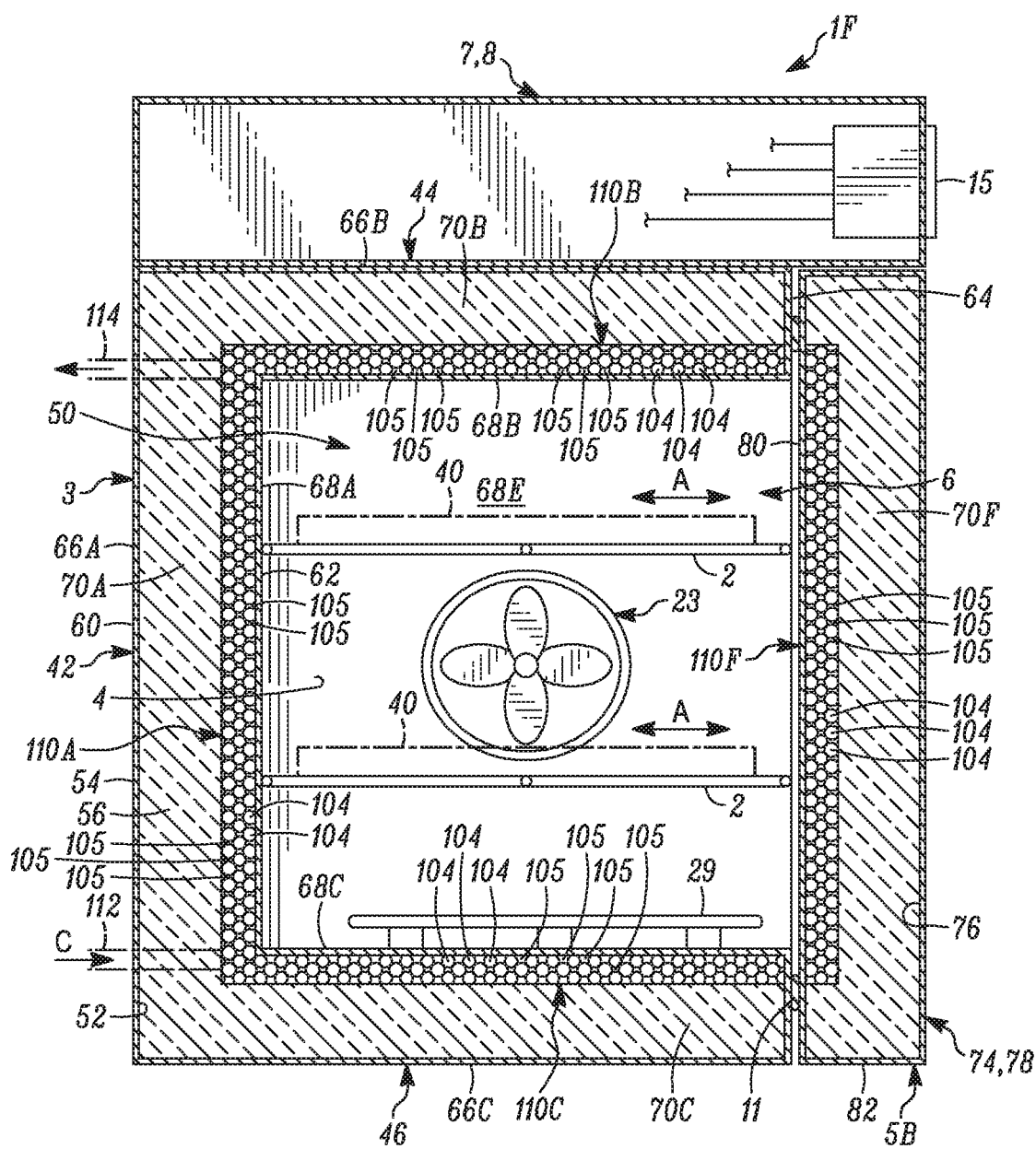
FIG. 11 is a sectional view similar to FIG. 5 of a seventh embodiment of the chamber of the present invention wherein the phase change material is contained within numerous encapsulated pellets which are within a liquid medium.
Figure 13:
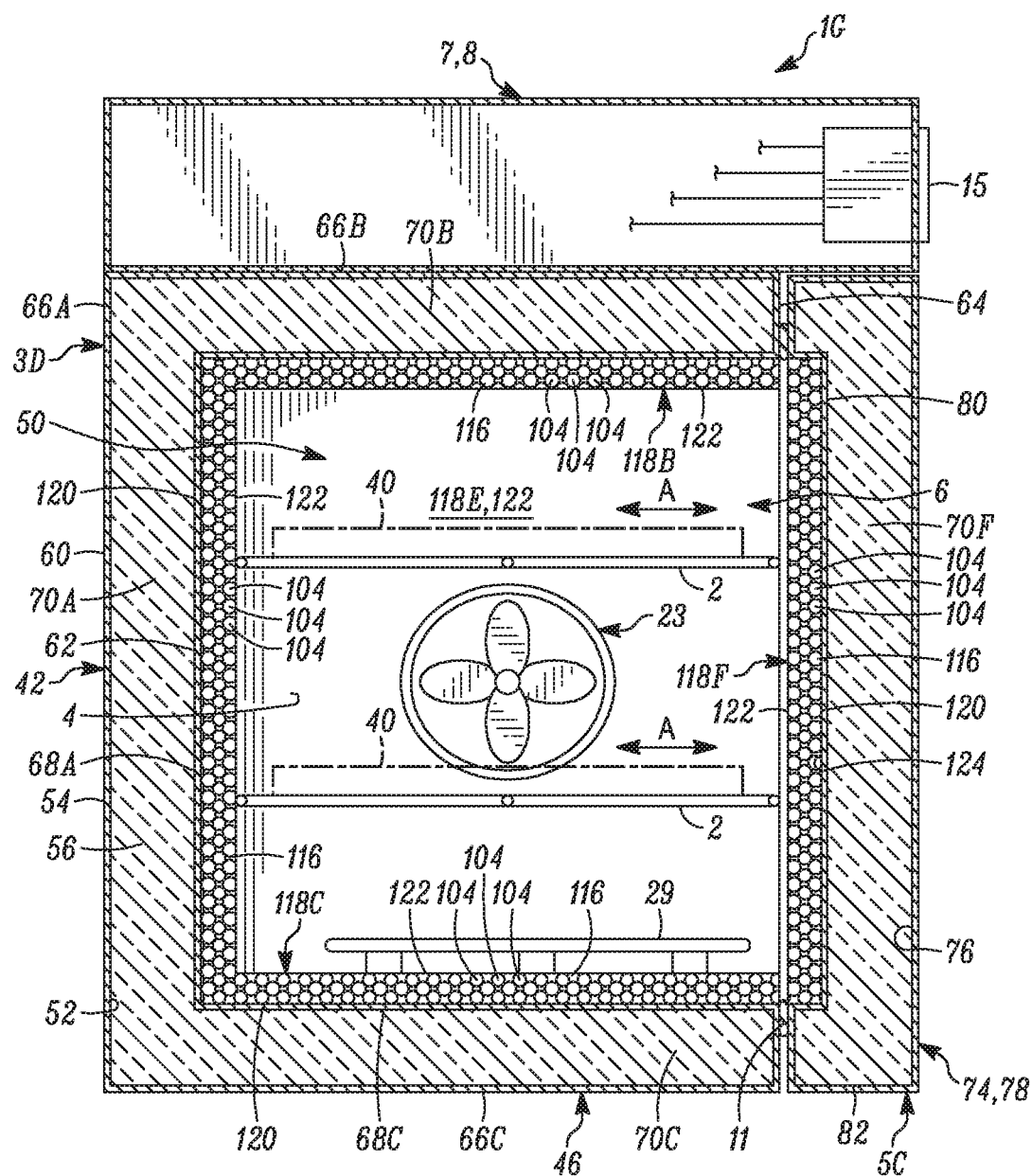
FIG. 13 is a sectional view similar to FIG. 12 of an eighth embodiment of the chamber of the present invention showing the phase change material within encapsulated pellets which are embedded in a solid matrix.
Figure 15:
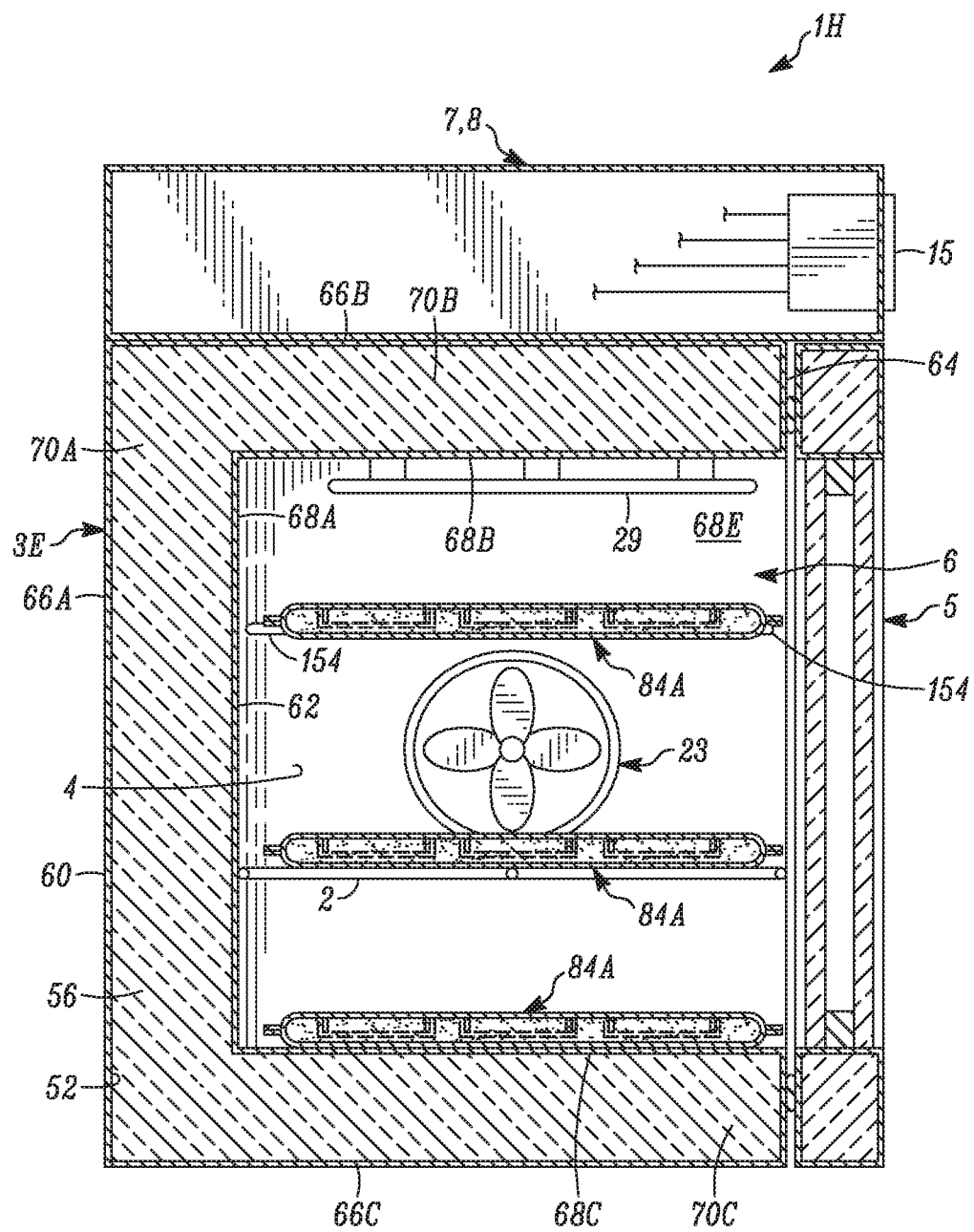
FIG. 15 is a sectional view similar to FIG. 7 of a ninth embodiment of the chamber of the present invention using the PCM packets or shelves shown in FIG. 14.

A first embodiment of the insulated enclosure or chamber of the present invention is shown generally at 1 in FIG. 1, with additional embodiments shown generally at 1A in FIG. 5, at 1B in FIG. 7, at 1C in FIG. 8, at 1D in FIG. 9, at 1E in FIG. 10, at 1F in FIG. 11, at 1G in FIG. 13, and at 1H in FIG. 15. Chamber 1 is configured to serve as an incubator, environmental chamber, oven, refrigerator or freezer. Chamber 1 includes a main body or container 3, a storage interior chamber 4 defined by container 3, a door 5 and a control assembly 7 secured to and seated atop container 3. Container 3 in the exemplary embodiment is in the form of a five-sided or five-walled box-like structure wherein the forward terminal ends of four of these walls define an entrance opening 6 (FIG. 2) of interior chamber 4. Upper and chamber 4. Upper and lower horizontal shelves 2 are disposed within interior chamber 4 extending between three of the walls of container 3 and suitably supported therein for supporting thereon one or more storage items 40 (dashed lines) to be stored in interior chamber 4 over a duration typically measured in hours, days, or weeks. Storage item 40 may, for example, be one or more petri dishes or other containers for growing cultures or for supporting other items which need incubation or heating in a controlled manner. Storage item 40 may also include the contents of a dish or container, such as a culture, and may include other components, some of which are discussed in greater detail further below. Item 40 may also be cooled in a controlled manner and frozen if desired. Insulated chamber is configured to heat and/or cool item 40 and/or to maintain item 40 within interior chamber 4 at a desired temperature, as described further below. Door 5 is hingedly attached to container 3 by hinges 9 to swing between open (FIG. 1) and closed (FIGS. 2, 4) positions. An annular sealing gasket 11 provides a seal between door 5 and container 3 when door 5 is closed, such that main body 3 and door 5 together form a six-sided or six-walled container or enclosure. Items 40 are removable from and insertable into (Arrows A in FIGS. 2, 5 7-11 and 13) interior chamber 4 through entrance opening 6 when door 5 is open.

Door 5 includes a transparent window 12 which may be double paned (FIG. 2) with two parallel panes 16 (typically made of glass) with an annular elastomeric seal 18 there between and in contact therewith to separate panes 16 by a space 20. Space 20 is defined by the inner perimeter of seal 18 and panes 16 and is filled with gas or under vacuum to help thermally insulate interior chamber 4 when door 5 is closed to cover entrance opening 6. Door 5 includes a rectangular annular wall 10 which surrounds window 12 along its outer edges and is hollow and typically includes a metal skin which defines a rectangular annular insulated fully enclosed door interior chamber or compartment 13 with thermal insulation 14 therein which nearly or completely fills compartment 13.

Control assembly 7 includes an enclosure or housing 8 on which is mounted a manual control interface 15 and which houses a temperature control unit 17, a humidity control unit 19 and a carbon dioxide control unit 21. Interface 15 is in electrical communication with control units 17, 19 and 21, and also with a fan assembly 23 within or in communication with interior chamber 4 and an electric power source 25 outside housing 8. Temperature control unit 17 is in electrical communication with a temperature sensor 27 within or bounding interior chamber 4 and with an electric heating unit or device in the form of a heating coil 29 within interior chamber 4. Temperature control unit 17 is also in electrical communication with a cooling device or refrigeration assembly 28 which includes internal heat-exchanging pipes 30 and external components 32 which typically include external heat-exchanging pipes, a compressor, and an expansion valve such that the refrigeration assembly provides a typical refrigeration cycle whereby the refrigerant within the coils is capable of providing active cooling within interior chamber 4 via the internal coils 30 therein. Cooling and heating devices 28 and 29 serve as electrically powered temperature-altering devices for altering the temperature of interior chamber 4, items 40 and other components within chamber 4 and portions of the walls defining chamber 4. Humidity control unit 19 is in electrical communication with a humidity sensor 31 within or bounding interior chamber 4 and with an actuator such as a solenoid of a water control valve 33 which is in fluid communication with a water source 35. Thus, humidity control unit 19 is operatively connected to interior chamber 4 to control the amount of humidity within chamber 4. Carbon dioxide control unit 21 is in electrical communication with a carbon dioxide sensor 37 and an actuator such as a solenoid of a carbon dioxide control valve 39 which is in fluid communication with a carbon dioxide source 41. Thus, carbon dioxide control unit 21 is operatively connected to interior chamber 4 to control the level of carbon dioxide within chamber 4.

Main body or container 3 is now described in greater detail. Container 3 has several generally rigid walls or sidewalls including a flat vertical rectangular back wall 42, flat rectangular horizontal top and bottom walls 44 and 46 secured respectively to the top and bottom of back wall 42 and extending forward therefrom, and flat vertical left and right side walls 48 and 50 secured respectively to the left and right sides of back wall 42 and extending forward therefrom.

Left and right side walls 48 and 50 are also secured to and extend between the respective left and right ends of top and bottom walls 44 and 46. Walls 42-50 thus form a box or cup-shaped configuration defining interior chamber 4 such that walls 44-50 at their front ends define entrance opening 6. A fully enclosed sealed rectangular cup-shaped interior cavity or chamber 52 is formed within container 3 separate from interior chamber 4 and more particularly is defined by a substantially rigid skin 54 which is typically formed of metal although it may be formed of a plastic or other suitable material. Chamber 52 surrounds interior chamber 4 on five sides thereof. Wall or sidewall chamber 52 is sealed from external atmosphere and is nearly or completely filled by insulation 56 and a phase change material 58 (PCM), each of which is also in a substantially rectangular cup-shaped configuration corresponding to that of chamber 52. The phase change material 58 is disposed between the insulation and interior chamber 4 along the entire inner surface of insulation 56 and thus essentially completely surrounds interior chamber 4 on all five sides of container 3. Thus, each of walls 42-50 includes several layers or materials. Insulation 56 may be formed of a variety of insulation materials which remain in a solid state throughout the operation of the chamber and which are generally rigid or compressible. For example, insulation 56 may be fiberglass, styrofoam, or various types of foam boards or sheets, such as those formed from polystyrene, polyurethane, polyisocyanurate and the like. Some of these insulation boards are referred to commonly as polyiso boards. PCM 58 is discussed in greater detail further below. Although PCM 58 is shown on all five sides of container 3 entirely surrounding interior chamber 4, chamber 1 may also be formed with PCM 58 on only one, two, three or four sides of container 3 so that PCM 58 is adjacent chamber 4, but does not surround chamber 4.

Skin 54 includes a rectangular cup-shaped outer layer 60, a rectangular cup-shaped inner layer 62 and a rectangular annular front layer 64 which is substantially vertical and extends between the front of outer and inner layers 60 and 62. Outer layer 60 thus forms outer layers of each of the walls of container 3, namely vertical rear outer layer 66A of back wall 42, horizontal top outer layer 66B of top wall 44, horizontal bottom outer layer 66C of bottom wall 46, vertical left outer layer 66D of left side wall 48 and vertical right outer layer 66E of right side wall 50. Inner layer 62 similarly forms the inner layers of each of these walls, namely vertical front inner layer 68A of back wall 42, horizontal bottom inner layer 68B of top wall 44, horizontal top inner layer 68C of bottom wall 46, vertical right inner layer 68D of left side wall 48 and vertical left inner layer 68E of right side wall 50. Each of layers 66 and 68 is flat and rectangular.

Insulation 56 likewise makes up insulation layers of each of the five walls of container 3 which abut the respective outer layer 66 thereof and extend inwardly therefrom part of the way toward the respective inner layer 68 thereof. More particularly, insulation 56 includes a vertical flat rectangular insulation layer 70A of back wall 42 which abuts the front inner surface of outer layer 66A and extends forward therefrom, a flat rectangular horizontal insulation layer 70B of top wall 44 which abuts the lower inner surface of outer layer 66D and extends downwardly therefrom, a flat rectangular horizontal insulation layer 70C of bottom wall 46 which abuts the top inner surface of outer layer 66C and extends upwardly therefrom, a flat rectangular vertical insulation layer 70D of left side wall 48 which abuts the inner surface of outer layer 66D and extends inwardly to the right therefrom, and a flat rectangular vertical insulation layer 70E of right side wall 50 which abuts the left inner surface of outer layer 66E and extends inwardly to the left therefrom.

PCM 58 also forms respective PCM layers of each of the walls of container 3, namely a vertical flat rectangular PCM layer 72A of back wall 42 which extends between and is in contact with the front inner surface of insulation layer 70A and the rear surface of skin inner layer 68A, a flat rectangular horizontal PCM layer 72B which extends between and is in contact with the bottom inner surface of insulation layer 70B and the top surface of inner layer 68B, a flat rectangular horizontal PCM layer 72C which extends between and is in contact with the upper surface of insulation layer 70C and the lower surface of inner layer 68C, a vertical flat rectangular PCM layer 72D which extends between and is in contact with the inner surface of insulation layer 70D and the left surface of inner layer 68D, and a flat rectangular vertical PCM layer 72E which extends between and is in contact with the left inner surface of insulation layer 70E and the right surface of inner layer 68E. Each PCM layer 17 is thus disposed within a cavity or portion of interior chamber 52 between the corresponding inner layer of the skin and layer of insulation 70.

Chamber 1A (FIG. 5) is similar to chamber 1 except that it includes a door 5A which is somewhat different than door 5 although both doors are substantially rigid and serve as a wall or sidewall of the chamber 1 or 1A. Unlike door 5, door 5A does not include a transparent window which allows someone to view the contents of interior chamber 4 from outside the chamber without opening the door. Instead, door 5A is opaque and has a configuration similar to one of the walls of container 3 and is thus made of several layers. In particular, door 5A includes a substantially rigid skin 74 which is relatively thin and typically formed of metal and defines a fully enclosed vertical rectangular interior cavity or chamber 76 which is separate from chambers 4 and 52, which is sealed from external atmosphere and in which are disposed an insulation layer 70F and a PCM layer 72F. Skin 74 includes outer and inner vertical rectangular layers 78 and 80 and a rectangular annular perimeter layer 82 which extends between and is secured to the respective outer perimeters of outer and inner layers 78 and 80 such that layers 78-82 define therewithin chamber 76. Insulation layer 70F extends from the top to the bottom and from the left side to the right side of interior chamber 76. Insulation layer 70F also abuts the inner surface of outer layer 78 and extends inwardly and rearwardly therefrom and may contact the front inner surface of inner layer 80 along its outer perimeter although insulation layer 70F only extends part of the way towards inner layer 80 along a rectangular portion of door 5A which is directly in front of entrance opening 6. PCM layer 72F is a flat vertical rectangular layer which extends between and abuts the front surface of inner layer 80 and the rear surface of insulation layer 70F such that when door 5A is closed, PCM layer 72F entirely covers or spans the entrance opening 6 of interior chamber 4. PCM layer 72F is thus disposed within a cavity or portion of the sidewall or door interior chamber 76 defined between inner layer 80 and insulation layer 70F. PCM layer 72F is intended to be permanently disposed within chamber 76 and is thus not removable therefrom, just as the PCM layers 72A-E are not removable from interior chamber 52 of container 3.

Figure 6:
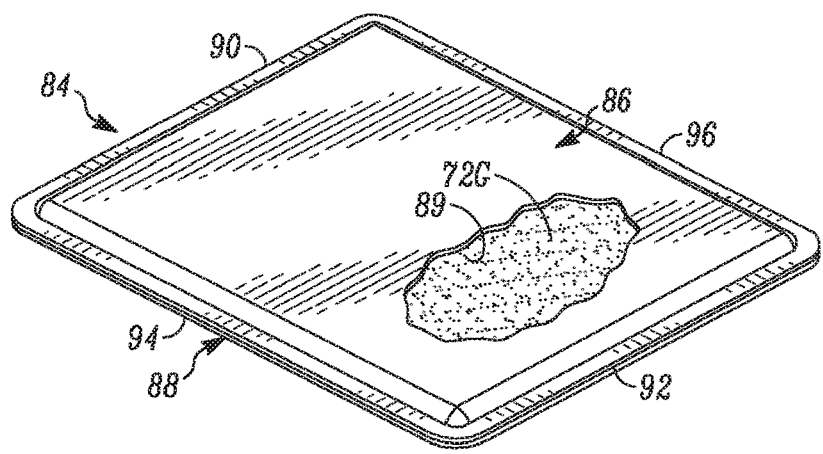
FIG. 6 is a perspective view with portions cut away of the removable and repositionable phase change material packet or wall of the present invention.

FIG. 6 illustrates a removable PCM packet 84 which is typically easily carried by one person and otherwise manipulated with one or two hands for use with chambers configured to receive packet 84. Packet 84 includes first and second substantially flat rectangular walls 86 and 88 which together form an outer skin and overlay one another such that their outer perimeters are superimposed and in contact with one another while the vast majority of walls 86 and 88 are spaced from one another to define there between a flat rectangular interior cavity or chamber 89 which receives therein a flat rectangular PCM layer 72G which nearly or completely fills chamber 89. Walls 86 and 88 are preferably formed of a substantially rigid thermally conductive material, such as a metal. Aluminum, stainless steel and copper are well suited for this purpose. However, walls 86 and 88 may be formed of a plastic or other suitable material. Packet 84 has first and second opposed straight parallel end edges 90 and 92, and first and second straight parallel opposed side edges 94 and 96 which extend respectively between end edges 90 and 92 so that edges 90-96 form a rectangular configuration along the outer perimeters of walls 86 and 88. Walls 86 and 88 are sealed to one another along each of edges 90-96 so that interior chamber 89 is fully enclosed and sealed from external atmosphere.

Chamber 1B is shown in FIG. 7 and utilizes removable PCM packets 84. Chamber 1B is similar to chambers 1 and 1A and is shown with door 5 although a door such as door 5A may also be used. Chamber 1B includes a container 3A which is similar to container 3 except that the insulation entirely or nearly entirely fills the interior chamber 52 since the PCM material is provided in packets 84 instead of within interior chamber 52. Thus, for example, the insulation layer 70A in the back wall of container 3A extends all the way from the front surface of outer layer 66A to the back surface of inner layer 68A. Similarly, insulation layer 70B extends continuously from the bottom surface of outer layer 66B to the top surface inner layer 68B, and insulation layer 70C extends all the way from the bottom surface of inner layer 68C to the top surface of outer layer 66C. The insulation layers in the two side walls of container 3A also extend all the way between the respective inner and outer layers thereof.

As shown in FIG. 7, the heating element 29 of chamber 1B is mounted on the top wall of container 3 within interior chamber 4 adjacent the top thereof. FIG. 7 further illustrates three of the removable PCM packets 84 within interior chamber 4. One of packets 84 is seated on top inner layer 68C of the bottom wall of container 3, which thus serves as a supporting structure or permanent shelf for the lower packet 84. Chamber 1B further includes a pair of horizontal trays 98 which respectively hang downwardly from the wire or other type shelves 2 such that each tray and the respective shelf are adjacent one another and define therebetween a respective rectangular flat horizontal packet-receiving space 100 for removably inserting therein a respective packet 84 through a front entrance opening of a respective space 100. Thus, the lowermost packet 84 is directly below the other two packets as well as directly below the two shelves and trays, and spaced downwardly from the lower tray. The middle packet 84 is thus seated atop the lower tray 98 below and adjacent the lower removable shelf 2. Similarly, the top or upper packet 84 is seated atop the upper tray 98 below and adjacent the removable upper shelf 2. In addition, the upper tray 98 is spaced upwardly from the lower shelf 2 so that a portion of interior chamber 4 is defined between the top of the lower shelf 2 and the bottom of tray 98 inasmuch as the upper tray 98 and the corresponding upper packet 84 is spaced upwardly from the lower shelf 2. This portion of interior chamber 4 receives petri dishes or other items 40 which are seated on the lower shelf 2 so that the temperature of item 40 and the environment in interior chamber 4 surrounding item 40 may be controlled. Items 40 are thus adjacent, above and out of contact with the respective packet 84 during the process of temperature and other environmental control in interior chamber 4. Similarly, interior chamber 4 includes an upper portion above the upper shelf 2 also configured to receive items 40, which are likewise adjacent, above and out of contact with the upper packet 84 during the process of thermal and other environmental control within interior chamber 4. As previously noted, each packet 84 may be inserted and removed from its respective space 100 or from atop the bottom wall (Arrows B in FIGS. 7, 8) through the entrance opening 6 when door 5 is open. Trays 98 serve as PCM packet shelves. However, PCM packets 84 may also be seated on shelves 2 or another support so that items 40 may be seated directly on packets 84.

Chamber 1C (FIG. 8) is similar to the previous chambers and includes a container 3B which is similar to but somewhat modified from the earlier containers. The insulation within interior chamber 52 of container 3B is the same as that described with reference to the insulation within container 3A of chamber 1B. As shown in FIG. 8, the heating element 29 is mounted adjacent and above the bottom wall of the container within interior chamber 4 in the same manner as with chamber 1. Chamber 1C illustrates the use of two PCM packets 84 in a different orientation than that shown with chamber 1B. A tray 98 is mounted on the top wall of container 3B within the upper portion of interior chamber 4 so that the upper PCM packet may slide horizontally (Arrow B in FIG. 8) to be inserted or removed from the space 100 above tray 98 and below and adjacent the top wall of container 3B. The 3B. The other packet 84 is positioned in a vertical orientation behind removable shelves 2 abutting or adjacent the front inner surface of inner layer 68A of the back wall of container 3B. More particularly, a clip 102 is secured to the back wall adjacent the top wall of the container and clips or clamps the first end edge 90, which serves as the top of packet 84 in the vertical orientation in order to suspend packet 84 in this rearward position. As will be appreciated, any suitable mechanism may be used in order to secure packet 84 in its hanging position or a vertical position closely adjacent the back insulating wall. PCM packets 84 of insulated chamber 1B and 1C are positioned so that they do not hinder the insertion and removal of items 40 from interior chamber 4, that is, items 40 may be inserted and removed without moving PCM packets from their respective positions within chamber 4. In addition, packets 84 are configured so that PCM 72G (like the non-removable PCM 56 of chamber 1) is not visible to the end user of the insulated chambers 1B and 1C. Moreover, PCM packets 84 are configured and positioned in chamber 4 so that the space normally reserved for items 40 on shelves 2 (i.e., without the use of packets 84 or trays 98) is not substantially reduced, and in most cases the reduction in available space for items 40 is not significant enough to have any real impact. Thus, the items 40 normally placed in a chamber 4 of a given size may still be placed therein with the addition of trays 98 and/or packet(s) 84. Although not shown, it is contemplated that a packet 84 may be positioned in a space behind or adjacent a "false" wall within chamber 4 such that the packet is hidden and whereby heat transfer to and from the packet is largely by convection. For example, such a false wall may be situated in front of the vertical packet 84 shown in FIG. 8.

Chamber 1D (FIG. 9) is similar to the previous chambers and includes a modified container 3C such that the interior chamber 52 contains insulation, PCM, and a heating element 29A sandwiched therebetween. The insulation layer 70C of chamber 1D is substantially the same as that described with regard to the chambers 1B and 1C in FIGS. 7 and 8.

Figure 2:
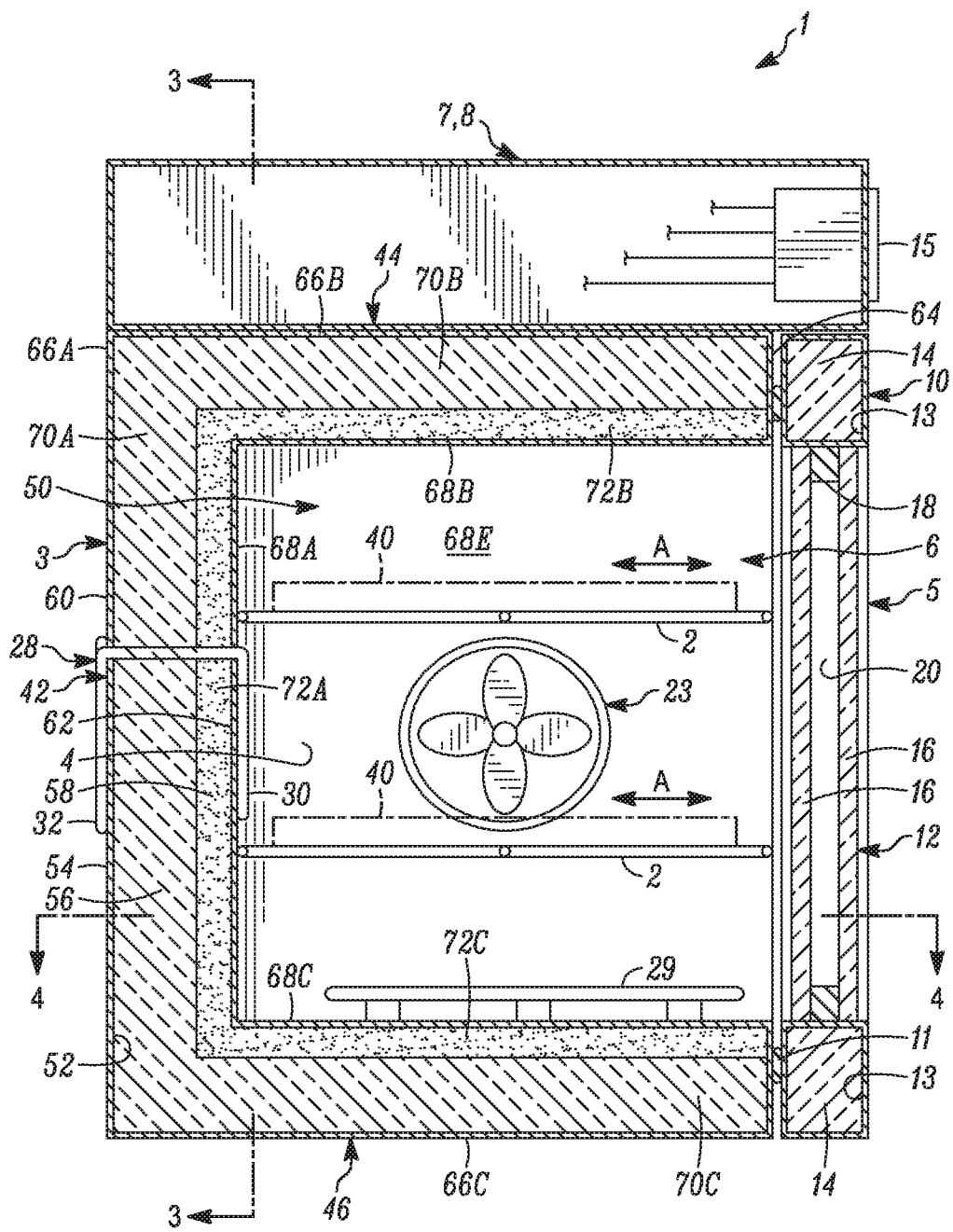
FIG. 2 is a sectional view taken on Line 2-2 of FIG. 1.
Figure 3:
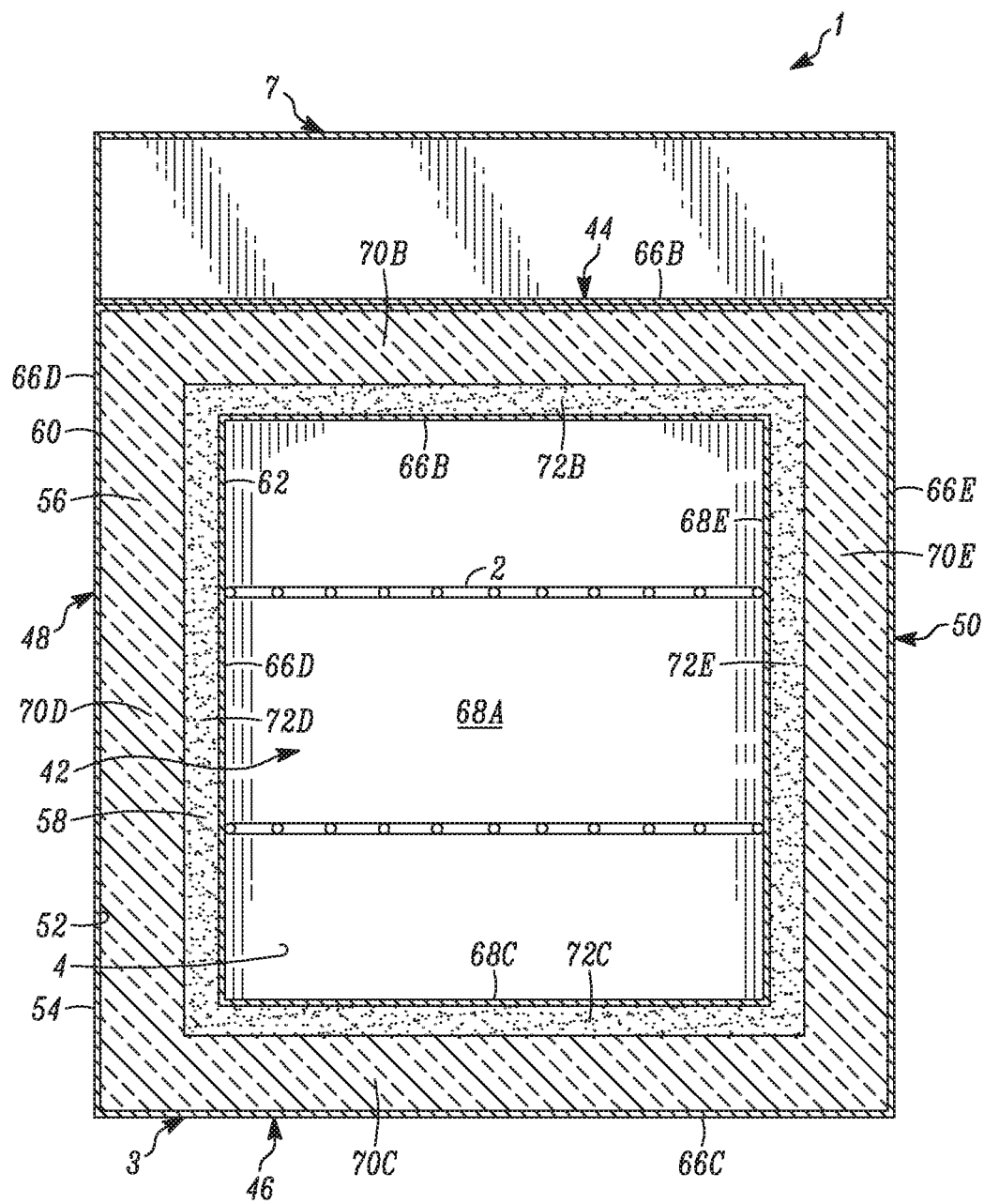
FIG. 3 is a sectional view taken on Line 3-3 of FIG. 2.

Similarly, the insulation in the left and right side walls of container 3C completely or nearly fills the portions of chamber 52 within the respective left and right side walls of container 3C. The insulation layers 70A and 70B of container 3C are substantially the same as those of chamber 1, as illustrated in FIGS. 2 and 3. In addition, the PCM layers 72A and 72B within container 3C are substantially the same as that shown and described with reference to FIGS. 2 and 3 of chamber 1. In chamber 1D, only these two PCM layers 72A and 72B are used such that the bottom wall and left and right side walls of container 1D do not include such PCM layers. As FIG. 9 illustrates, interior chamber 4 is free of a heating element such as heating element 29 of the previous embodiments. Instead, heating element 29A is sandwiched between insulation layer 70A and PCM layer 72A and is thus substantially vertically oriented and in contact with each of said layers. Element 29A is thus entirely external to interior chamber 4.

Chamber 1E (FIG. 10) is similar to chamber 1D except that it includes a heating element 29A which is sandwiched between PCM layer 72A and inner layer 68A. Element 29A is thus in contact with the rear surface of layer 68A and the front surface of PCM layer 72A.

Figure 12:
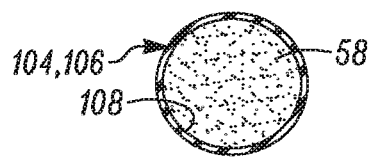
FIG. 12 is a sectional view of one of the encapsulated pellets.

Chamber 1F (FIG. 11) is similar to chamber 1A (FIG. 5) except that the various layers 72 of PCM 58 are replaced by numerous encapsulated PCM pellets 104 and a liquid medium 105 in which the pellets 104 are disposed. As shown in FIG. 12, each pellet 104 includes a solid capsule 106 having an inner surface which defines an interior chamber 108 or an enclosure which is sealed from the external atmosphere or environment by the solid skin or capsule 106. Interior chamber 108 is nearly or completely filled with PCM 58. As shown in FIG. 11, the mixture of pellets 104 and medium 105 form layers 110 which include a substantial amount of PCM 58 and are analogous to layers 72. While layers 110 may be on all sides of interior chamber 4, FIG. 11 shows only layers 110A, 110B, 110C and 110F, which are respectively analogous to layers 72A, 72B, 72C and 72F. Typically, pellets 104 are packed in as tightly or nearly as tightly as they can within the portion of interior chamber 52 defined between insulation 56 and inner layer 62 of skin 54. Pellets 104 are similarly packed into the portion of interior chamber 76 of the door between the insulation layer 70F and inner layer 80 of skin 74. Pellets 104 define therebetween interstitial spaces which are typically completely or nearly filled by liquid medium 105. Although in the exemplary embodiment, medium 105 is in a liquid form, it may also be in a gaseous form. In any case, the interior chamber 52 is completely or nearly filled by insulation 56, pellets 104 and medium 105. Similarly, the interior chamber 76 of the door is nearly or completely filled with insulation 70F, pellets 104 and medium 105.

As shown in dashed lines in FIG. 11, chamber 1F may include an inlet 112 and an outlet 114 communicating with the portion of interior chamber defined between insulation 56 and inner layer 62 of skin 54 such that a liquid or a mixture of pellets 104 and liquid medium 105 may be pumped or otherwise moved into this portion of the interior cavity via inlet 112 (arrow C) and out of this portion of the interior cavity through outlet 114 (arrow D). The provision of an inlet and an outlet is one manner of filling this portion of the interior chamber 52 with pellets 104 and medium 105, and also would allow for the pellets and medium to be removed via outlet 114 and, if desired, replaced with another set of pellets and liquid medium in which the PCM 58 of the pellets has a different melting or freezing temperature than that of the original pellets. It is noted that liquid 105 may be a phase change material which serves in the same fashion as PCM 58, or it may remain in a liquid state within the operational parameters of chamber 1F. The illustration with the use of inlet 112 and outlet 114 may represent the type of insulated chamber which uses a water jacket. Thus, instead of using the water jacketed insulated chamber in the standard manner, pellets 104 and liquid medium 105 may instead be used to fill the interior chamber of the water jacket in order to utilize the advantage of PCM 58 of the present invention.

Chamber 1G (FIG. 13) is similar to chamber 1F in that it also utilizes PCM pellets 104. However, instead of pellets 104 being disposed within liquid medium 105, pellets 104 of chamber 10 are embedded in a solid matrix 116. More particularly, the matrix 116 and embedded pellets 104 form respective flat rectangular layers 118 which are analogous to PCM layers 72A-F and layers 110 such that each of the layers is flat and rectangular and either horizontal or vertical as previously discussed with respect to layers 72. FIG. 13 shows specifically layers 118A-C, 118E and 118F. However, unlike layers 72 and layers 110, layers 118 are in the exemplary embodiment not within the interior chamber 52 defined by skin 54 of such chambers as chamber 1, 1A and 1F. Although layers 118 could be positioned within chamber 52 in the analogous positions of layers 72 and 110, the use of layers 118 illustrates one manner of forming layers comprising PCM 58 wherein the layers are external to interior chambers 52 and 76. Thus, chamber 1G may include a container 3D and a door 5C each of which has a somewhat different configuration than those of the previous embodiments. Container 3D retains skin 54 and its various layers to define there within the interior chamber 52. However, insulation 56 itself either completely or nearly fills interior chamber 52. FIG. 13 shows that inner layers 68 of skin 54 are positioned closer to the corresponding outer layers 68 such that outer layers 66 abut the outer surface of insulation 56 and the inner layer 68 abut the inner surface of insulation 56. Thus, insulation 56 in FIG. 13 appears to have the same thickness as insulation 56 in FIG. 11. However, the inner and outer layers 66 and 68 may also be spaced apart from one another as in the previous embodiments such that insulation 56 still fills the entire chamber 52 and is thicker, as shown in FIG. 7. Each of layers 118 has an outer surface 120 and an inner surface 122.

Each outer surface 120 of a given layer 118 which is part of container 3D abuts an inner surface of a corresponding inner layer 68 so that each layer 118 extends inwardly therefrom to inner surface 122. Thus, for instance, outer surface 120 of layer 118A is vertical and abuts the vertical inner surface of back inner layer 68A and extends inwardly therefrom to vertical surface 122 of layer 118A. The outer surface 120 of layer 118B serves as a top surface which thus abuts the inner or bottom surface of top inner layer 68B so that layer 118B extends downwardly therefrom to the horizontal inner or bottom surface 122 thereof. The outer surface 120 of layer 118C thus serves as a bottom horizontal surface from which layer 118C extends upwardly to the inner or top horizontal surface 122 thereof. The left and right walls of container 3D are formed in a similar manner to the back wall thereof such that the corresponding layer 118 is vertical, and the inner and outer surfaces 120 and 122 of the corresponding vertical layers 118 (layer 118E shown in FIG. 13) are vertical and oriented such that the outer layer 120 abuts the corresponding inner layer 68 and extends inwardly therefrom to the vertical inner surface 122. Thus, the inner surfaces 122 of the layers 118 define interior chamber 4, unlike the earlier embodiments in which the inner layers 68 of skin 54 defined interior chamber 4.

Although door 5C is similar to the doors of the earlier embodiments, it also differs somewhat in that inner layer 80 defines a vertical flat rectangular recess 124 in which layer 118F is received with its vertical outer or front surface 120 abutting the vertical inner surface of layer 80 and extending forward therefrom to the flat vertical inner or rear surface 122, which bounds interior chamber 4 when door 5C is closed. Although layer 118F is shown disposed in recess 124, a layer similar to 118F may be mounted on a door without such a recess and thus project forward beyond the forward most portion of the inner skin.

In the exemplary embodiment, solid matrix 116 is typically formed of a cured resin. Thus, during formation of layers 118, the original material which ultimately becomes matrix 116 is a liquid resin or in liquid form and thus cures to form the solid resin. In one embodiment, pellets 104 are mixed into a paint, which can then be painted onto any given surface, such as the inner layer 62 and the inner layer 80 and then allowed to dry. Paints typically contain a resin and a solvent, such that when the solvent dries, the resin is allowed to cure by chemical reaction. Some paints are also thermosetting, meaning that they are also heated in order to cure the resin. In another embodiment of solid matrix 116, the resin may not include a solvent which needs to dry in order to cure. For example, some resins are simply heat cured from a liquid state to a solid state without or with extremely minimal evaporation of components making up the liquid resin. Other liquid resins may be light cured in order to reach the solid state.

Thus, the layers 118 may be formed in several different ways. Where the matrix and its liquid form is a paint, the paint with pellets 104 mixed into it may simply be painted onto a given desired surface and allowed to dry. Another option is to pour a given liquid resin with the pellets 104 mixed therein into a cavity or recess such as recess 124 (such as when door 5C is laid horizontal with the recess 124 facing upwardly), and either allowed to dry, as with the paint, or cured by heat, light or any other suitable method in order to cure the resin within the recess. Alternately, any of the layers 118 may be independently formed in a mold cavity and subsequently mounted in the positions shown in FIG. 13 by any suitable mechanism. For instance, the bottom layer 118C may simply be laid atop the inner layer 68C, or may be adhered with a glue or another adhesive thereto. The other layers 118 may similarly be adhered by a glue or an adhesive or so forth. Further, the various layers 118 of container 3D may be formed as a single cup-shaped piece. Such formations may be done in a separate mold, or may use the inner layer 62 of skin 54 to define a portion of the mold. Matrix 116 may have varying degrees of thermal conductivity. The thermal conductivity may be enhanced by incorporating metal chips or other materials which are highly thermally conductive into the liquid resin during formation of the layers 118.

Figure 14:
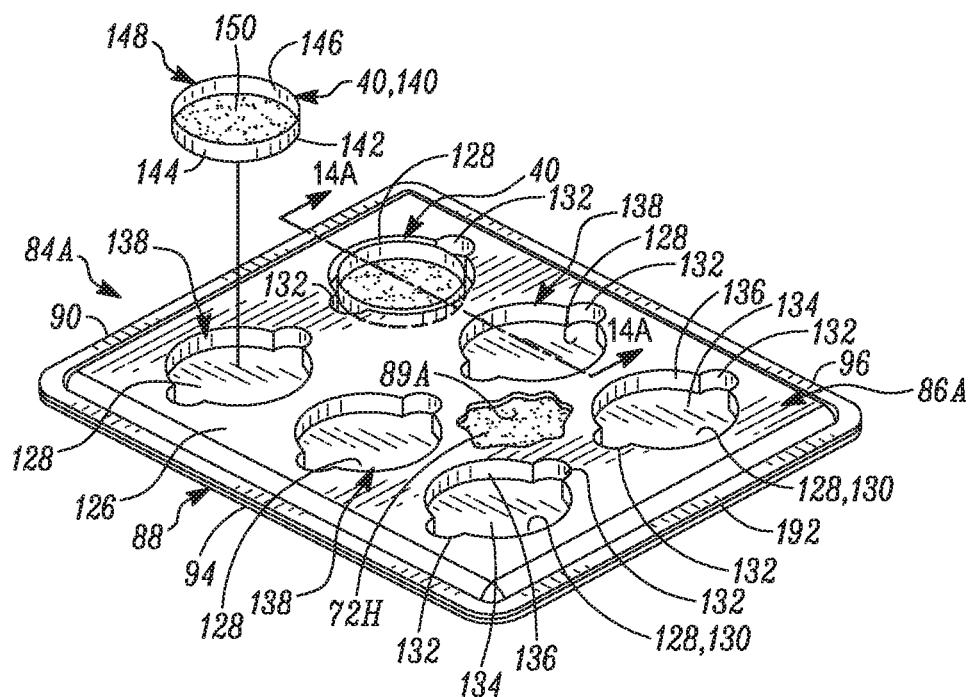
FIGS. 14 and 14A are perspective views of a PCM packet or shelf having recesses formed therein for receiving respective storage items.

FIG. 14 shows another PCM packet or shelf 84A which is similar to packet 84 shown in FIG. 6. Shelf 84A thus includes generally flat rectangular bottom wall 88 and a generally flat rectangular top wall 86A which define therebetween an interior chamber 89A which is filled with a layer 72H of PCM. PCM layer 72H typically completely or nearly fills interior chamber 89A. It is noted that PCM layer 72H of packet 84A or PCM layer 72G of packet 84 (FIG. 6) may be replaced with pellets 104, along with a gas or liquid medium 105 (FIG. 11) or embedded in solid matrix 116 (FIG. 13). Walls 86A and 88 are formed of the same materials as previously described with regard to packet 84, and are joined to one another to form end edges 90 and 92, and side edges 94 and 96. Unlike wall 86 of packet 84, which is substantially flat in a continuous manner from adjacent edge 90 to adjacent edge 92 and from adjacent edge 94 to adjacent edge 96, wall 86A includes an upper flat portion 126 which extends from adjacent edge 90 to adjacent edge 92 and from adjacent edge 94 to adjacent edge 96, but is interrupted by a plurality of recesses 128 extending downwardly therefrom. In the exemplary embodiment, packet 84A includes six recesses 128 although the number may vary depending on the size of the packet and the specific need. Although recesses 128 may be of any desired shape, each recess 128 is shown with a circular central portion 130 and a pair of opposed finger receiving portions 132 which extend laterally outwardly from central portion 130 on opposite sides thereof and away from one another. The bottom of each recess 128 is defined by a flat horizontal recessed wall 134 which is spaced downwardly from upper flat portion 126. An annular side wall 136 at its lower end is rigidly secured to and extends upwardly from the outer perimeter of recessed wall 134 to a rigid connection at its upper end to upper flat portion 126, whereby each recessed wall 134 and the corresponding side wall 136 defines the corresponding recess 128. Each recess 128 has a top entrance opening 138 through which a given storage item 40 may be downwardly inserted and upwardly removed, as indicated at arrow E in FIG. 14.

With continued reference to FIG. 14, the specific storage item 40 includes a container or petri dish 140 having a flat circular bottom wall 142 and a circular annular side wall 144 rigidly secured to and extending upwardly from the bottom wall 142 to define there within a cylindrical cavity 146 with a top entrance opening 148. Cavity 146 is thus configured to receive various contents via entrance opening 148 and/or have the contents removed thereby. In the exemplary embodiment, item 40 includes the contents, which are in the form of a culturing medium 150 with living cells 152 to be grown or cultured thereon.

Figure 14A:
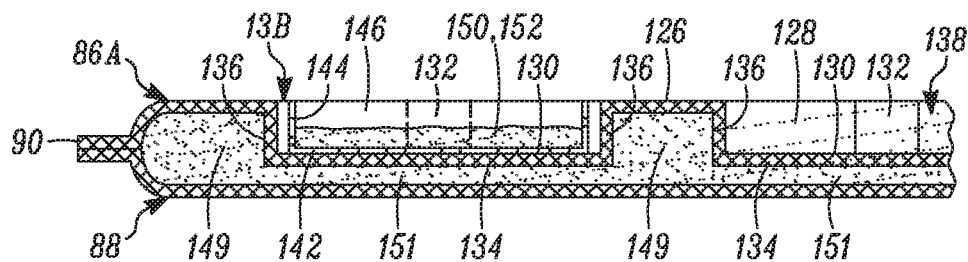

The sectional view of FIG. 14A illustrates the relative positions of the petri dish 140 and its contents to the corresponding recess 128 and various components of the packet 84A, including the PCM. The PCM of layer 72H includes a lateral portion or portions 149 which may also be referred to as a recess-surrounding portion. The PCM of layer 72H also includes respective sub-recess portions 151 which are located directly below the corresponding recess 128 and recessed wall 134. The lateral portions 149 extend laterally outwardly from annular side wall 136 in all directions so that this portion of the PCM, as viewed from above, surrounds the corresponding annular side wall 136, as well as the bottom wall 134, recess 128, and when petri dish 140 is disposed within 128, also the bottom wall 142 thereof, at least a portion of side wall 144, and all or part of medium 150 and cells 152. Portions 149 have a top surface which abuts the bottom surface of upper flat portion 126 whereby the PCM of layer 72H extends from below recessed wall 134 and the bottom of petri dish 140 to above recessed wall 134, bottom wall 142, most or all of side wall 144 and all or part of medium 150 and cells 152. In the exemplary embodiment, bottom wall 142 of dish 140 is seated on horizontal flat recessed wall 134 with annular side wall 144 abutting or closely adjacent annular side wall 136, which typically has a substantially similar shape as side wall 144 as viewed from above so that the petri dish side wall and the contents of the dish are adjacent portions 149 of PCM. In the exemplary embodiment, the top of the petri dish is no higher than the top of the top of upper flat portion 126 although this may vary. Likewise, the medium 150 and cells 152 are typically no higher than the top of portion 126.

Referring now to FIG. 15, chamber 1H is configured to use the packets or shelves 84A shown in FIG. 14. Chamber 1H is similar to chamber 1B shown in FIG. 7 except that chamber 1H shows a different shelving configuration. FIG. 15 illustrates that the lower packet or shelf 84A is removably positioned atop inner layer 68C of the bottom wall, similar to the lower packet 84 in FIG. 7. However, the middle packet or shelf 84A is seated atop a wire or other shelf 2 rather than on a tray 98 as in FIG. 7. The bottom walls 88 of each of the lower and middle shelves or packets 84A are atop a supporting surface or shelf whereby each packet 84A serves as a shelf on which the various items 40 are seated within interior chamber 4. The upper shelf 84A of chamber 1H is supported within interior chamber 4 in a different manner. More particularly, support ledges 154 are connected to and extend inwardly from the left and right walls defining interior chamber 4 in order to support the upper packet 84A respectively along its left and right side edges 94 and 96. FIG. 15 shows only one of support ledges 154, which extends from adjacent the back of interior chamber 4 to adjacent the front of interior chamber 4. Thus, packet 84A along the left and right edges 94 and 96 form respective lips which are seated on the support ledges 154. These lips or side edges of packet 84 easily slide along support ledges 154 to insert the packet or shelf 84A into chamber 4 or remove it therefrom via entrance opening 6 when door 5 is opened.

Figure 17:
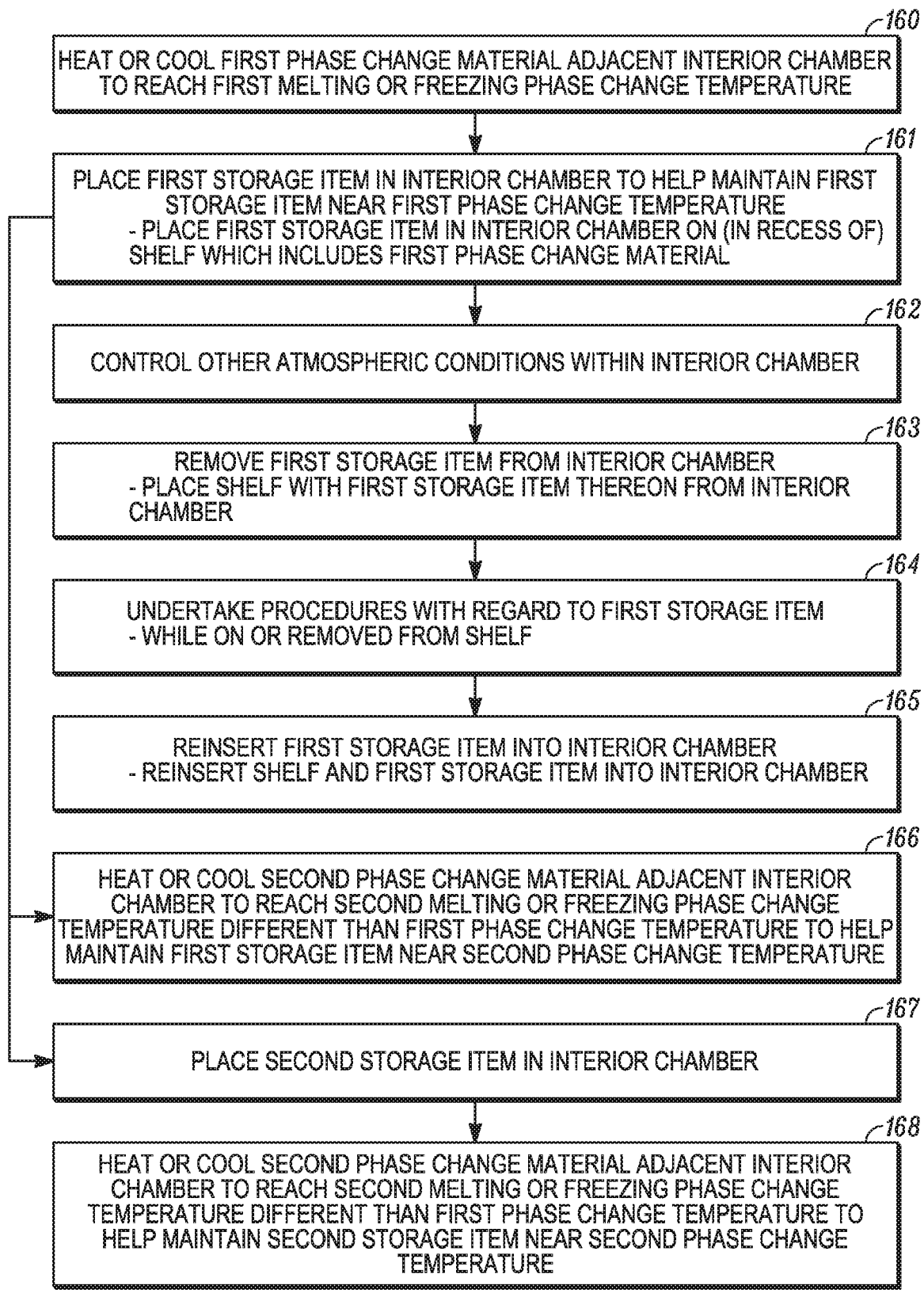
FIG. 17 is a flow chart illustrating various methods of the present invention. Similar numbers refer to similar parts throughout the drawings.

Although each of the chambers described above vary somewhat from one another, all of them operate in essentially the same basic manner. Various processes of the present invention are illustrated in the flow chart of FIG. 17 at blocks 160-168 and will be referred to hereafter although not necessarily in the same order. Each insulated chamber is configured to control various atmospheric conditions within interior chamber 4 (block 162). For example, power source 25 provides the power for running the various electrical components of chamber 1, such as fan assembly 23, control units 17, 19, and 21, refrigeration assembly 28, heating unit 29 and the solenoid or other actuator of control valves 33 and 39. The user of chamber 1 manipulates the settings of temperature, humidity and $CO_2$ level within interior chamber 4 via control interface 15, which may include three or more buttons or controls as shown in FIG. 1 which correspond respectively to these three features. Sensors 27, 31 and 37 respectively sense or determine the temperature, humidity and $CO_2$ level within interior chamber 4 and produce respective signals which are sent respectively to temperature control unit 17, humidity control unit 19 and $CO_2$ control unit 21. Based on the signal from temperature sensor 27, temperature control unit 17 controls heating unit 29 to turn it off, turn it on and/or control the degree of heat produced thereby for providing heat within interior chamber 4 as well as heat to PCM material 58 radiated through the various inner layers 68 of skin 54. Temperature control unit 17 may also control refrigeration assembly 28 in response to the signal from temperature sensor 27 to control the degree of cooling provided thereby within interior chamber 4, such as by turning it off or turning it on. Based on the signal from humidity sensor 31, humidity control unit 19 controls the solenoid or other actuating mechanism for operating control valve 33 to increase or decrease the amount of moisture within interior chamber 4. Similarly, based on the signal from $CO_2$ sensor 37, $CO_2$ control unit 21 controls the solenoid or other actuating mechanism of control valve 39 in order to increase or decrease the amount of carbon dioxide entering interior chamber 4 in order to provide the appropriate level of $CO_2$ in accordance with the input settings. Fan assembly 23 may be operated to rotate the fan in order to gently blow the gas within interior chamber 4 to maintain a substantially uniform temperature, humidity and level of carbon dioxide throughout the chamber. Fan assembly 23 may be operated on a continuous basis or intermittently in a variety of predetermined patterns, which may be related to the opening and closing of door 5, especially to help recover the internal temperature and the $CO_2$ and humidity levels after the door has been opened and closed.

PCM 58 of the present invention helps to maintain interior chamber 4 at a substantially constant temperature due to the significant amount of latent heat which PCM 58 absorbs or releases during its phase change, namely melting or freezing. PCM 58 is especially helpful in maintaining that temperature if there is a loss of power to the heating element 29 or refrigeration assembly 28 for an extended period. More particularly, PCM 58 is configured to have a melting or freezing phase change temperature which is at or about a desired selected temperature of interior chamber 4. Thus, the storage item or items 40 may be placed in interior chamber 4 to help maintain the storage items near the phase change temperature of a given PCM 58 (block 161). Typically, the melting or freezing temperature of PCM 58 is within the range of about −40.degree. C. (−40.degree. F.) to about 150.degree. C. (302.degree. F.) or 160.degree. C. (320.degree. F.). However, the melting or freezing temperature of PCM 58 may be less or greater than this range.

In one embodiment, the melting temperature of PCM 58 is about 37 degrees C. (98.6 degrees F.) since this is one of the most commonly used temperatures for culturing bacteria and mammalian cells. One suitable phase change material which has a melting or freezing temperature of about 37 degrees C. is available under the trade name "BioPCM Phase Change Material-37" from Phase Change Energy Solutions, Inc. of Asheboro, N.C. For maintaining temperatures above ambient, this PCM releases heat as it transitions from a liquid phase to a solid phase. This situation is desirable when power has been removed from the incubation chamber as the heat released by the PCM maintains the temperature of the chamber interior space. For applications where cold temperatures are desirable within an interior space, the PCM absorbs heat while transitioning from a solid to a liquid phase.

This BIOPCM product includes a phase change component and a fire suppression component. The phase change component is a derivative of fatty acids. Phase Change Energy Solutions, Inc. also produces PCMs that have respective melting or freezing temperatures anywhere within the range of about −40 degrees C. to about 150 degrees C. or 160 degrees C. Similarly, phase change materials which are suitable for use as PCM 58 in the present invention are available from Entropy Solutions, Inc. of Minneapolis, Minn. Entropy Solutions, Inc. also produces a large variety of PCMs which have a respective melting temperature within the range of about −40.degree. C. to about 150.degree. C. or so. For example, one such PCM which melts or freezes at about 37 degrees C. is available from Entropy Solutions, Inc. under the name "PureTemp 37." Likewise, Entropy Solutions, Inc. produces other PCMs, such as "PureTemp −40" having a melting point of about −40.degree. C., "PureTemp −12" having a melting point of about −12.degree. C., "PureTemp 4" having a melting point of about 4 degrees C., "PureTemp 23" having a melting point of about 23 degrees C., "PureTemp 30"

having a melting temperature of about 30 degrees C., "PureTemp 40" having a melting point of about 40 degrees C. and "PureTemp 50" having a melting point of about 50 degrees C. This company also produces a much wider variety of PCMs, for example PCMs (with analogous names) which have melting or freezing points respectively of about −14 degrees C., about 7 degrees C., about 7 degrees C., about 15 degrees C., about 18 degrees C., about 27 degrees C., about 30 degrees C., about 43 degrees C., about 48 degrees C., about 53 degrees C., about 55 degrees C., about 56 degrees C., about 61 degrees C., about 68 degrees C., about 103 degrees C., and about 151 degrees C. Entropy Solutions, Inc. is capable of producing a PCM of substantially any desired melting temperature. Entropy Solutions, Inc. indicates that the PCMs which they produce are from vegetable-based fats and oils. It is noted, however, that any suitable phase change material having the desired melting temperature may be used as PCM 58.

In some cases, it is desired to maintain the temperature of interior chamber 4 and item 40 at a temperature higher than room temperature (about 22 to 23 degrees C. or 71 to 73 degrees F.) or the ambient temperature, and thus PCM 58 is a solid at room temperature or at the ambient temperature. To take advantage of the phase change concept of such an embodiment of material 58, heating element 29 is operated in order to heat interior chamber 4 and the phase change material 58 until it melts at its melting phase change temperature (block 160). Most preferably, all of PCM 58 is melted so that PCM 58 is able to provide the greatest duration of substantially constant temperature during its phase change from the liquid state to the solid state while there may be no additional heat source available to maintain the interior temperature of interior chamber 4, such as during a power outage. In the heating scenario, each of the chambers positions the phase change material between the solid insulation and interior chamber 4, or positions the phase change material within interior chamber 4 itself so that insulation 56 of the container and the insulation of door 5A and/or the double paned window of door 5 substantially aids in preventing loss of heat from interior chamber 4.

In other cases, it is desired to maintain the temperature of interior chamber 4 and item 40 at a temperature lower than room temperature or the ambient temperature, and thus PCM 58 is a liquid at room temperature or at the ambient temperature. Thus, refrigeration assembly 28 is operated in order to cool interior chamber 4 and the phase change material 58 to its freezing point or phase change temperature so that it freezes or solidifies (block 160). Most preferably, all of PCM 58 is frozen or solidified so that PCM 58 is able to provide the greatest duration of substantially constant temperature during its phase change from the solid state to the liquid state while there may be no additional cooling or refrigeration source available to maintain the interior temperature of interior chamber 4, such as during a power outage. In the refrigeration scenario, the phase change material in the respective insulation chambers is positioned so that insulation 56 of the container and the insulation of door 5A and/or the double paned window of door 5 substantially aids in preventing the transfer of external heat into interior chamber 4.

Although PCM 58 is well suited to help maintain the temperature during a power outage, it also helps in a variety of other situations. For instance, PCM 58 helps maintain and/or expedite recovery of the desired temperature within interior chamber 4 during and after door 5 is opened (FIG. 1) such as when item or items 40 are inserted and/or removed from interior chamber 4 (Arrows A in FIGS. 2, 5, 7-11, 13). Further, PCM 58 helps maintain or expedite recovery of the desired temperature when the temperature in chamber 4 is otherwise changed (increased or decreased) due to such factors as electrical power fluctuations, gas injections such as injection of carbon dioxide via $CO_2$ control unit 21, liquid injections such as injection of water via humidity control unit 19, exothermic or endothermic reactions occurring within item or items 40, and electronic devices which are part of an item 40. Such an electronic device might be, for example, lighting equipment such as might be used to simulate sunlight for growing plants, such that the light would produce heat when turned on within chamber 4. Another type of such an electronic device is a water pump for pumping water through an aqua tank, such as used for growing algae. Other examples of such an electronic device are a shaker for agitating a solution to facilitate growth, or a cell roller for rolling a bottle back and forth. Any of these electronic devices or others would during operation produce heat which would likewise tend to heat chamber 4 and any item therein. In addition, turning such electronic devices off while in chamber 4 would reduce the amount of heat energy that the electronic device produced within chamber 4 and thus alter the temperature in chamber 4. Likewise, altering the operation of such electronic devices in particular ways may also change the amount of heat that the device produces within chamber 4 at a given time. PCM 58 thus helps to maintain and/or facilitate recovery of the desired chamber 4 temperature in all of these scenarios or any other situation which would affect the internal temperature of chamber 4.

PCM 58 enhances the ability to maintain the stability of the temperature within chamber 4 as well as the uniformity of the temperature throughout chamber 4. The use of PCM 58 also enhances humidity uniformity in chamber 4 in combination with the humidity controls of the insulated chambers of the present invention, such that a stable dew point can be created in chamber 4, and the formation of condensation on items within chamber 4 or the walls defining chamber 4 can be minimized or eliminated. While the usefulness of PCM 58 has been described primarily as being related to its phase change characteristics, it is worth noting that PCM 58 also acts as an effective thermal mass and/or a thermal insulator.

It is also noted that other than PCM 58 and possibly the liquid medium 105, the other components of the various insulated chambers of the present invention are not considered to be PCMs, but rather remain in a single state, typically solid, throughout the entire range of the operational parameters of the given insulated chamber. Thus, among the components that remain in a solid state over the entire operational parameter of the insulated chambers of the present invention are the skins of the container and door, the control assembly, the various layers of insulation 70 and the like, the various control units, sensors and control valves, the heating and cooling devices (other than the liquid refrigerant within the cooling device), glass panes of the door where used, the seals used between the panes and between the door and the container, the wire or other similar shelves, the outer skin of the PCM packets, the fan assembly, the solid matrix when used, and any other components which would obviously remain in a solid state during the normal operational parameters of the insulated chamber.

Although the various insulated chambers described herein are similar, the certain aspects of the configurations may be more suited to certain purposes. For example, the upper and middle packets 84 in chamber 1B (FIG. 7) are positioned below and adjacent the respective shelf 2 and item 40 thereon, which is better suited for when the desired temperature of chamber 4 and item 40 is above the ambient temperature. On the other hand, the upper packet 84 in chamber 1C (FIG. 8) is positioned above and adjacent the upper shelf 2 and upper item 40 thereon, which is better suited for when the desired temperature of chamber 4 and item 40 is below the ambient temperature. Generally, the PCM is distributed strategically to enhance natural convection, and thus more PCM is located toward the bottom of chamber 4 when the desired chamber 4 temperature and PCM melting temperature is above the ambient temperature, whereas more PCM is located toward the top of chamber 4 when the desired chamber 4 temperature and PCM melting temperature is below the ambient temperature. In addition, more PCM is typically positioned adjacent the door opening to offset the heat loss path created in this area. It is further noted that various of the thermally conductive materials used in the present invention enhance thermal conduction between the PCM and interior chamber 4 and between the PCM and components within chamber 4 including item 40. In particular, layers 86 and 88 of packet 84 enhance such thermal conduction, as do inner layer 62 of skin 54 (FIGS. 2, 3) and inner layer 80 of skin 74 of door 5A (FIG. 5).

Figure 16:
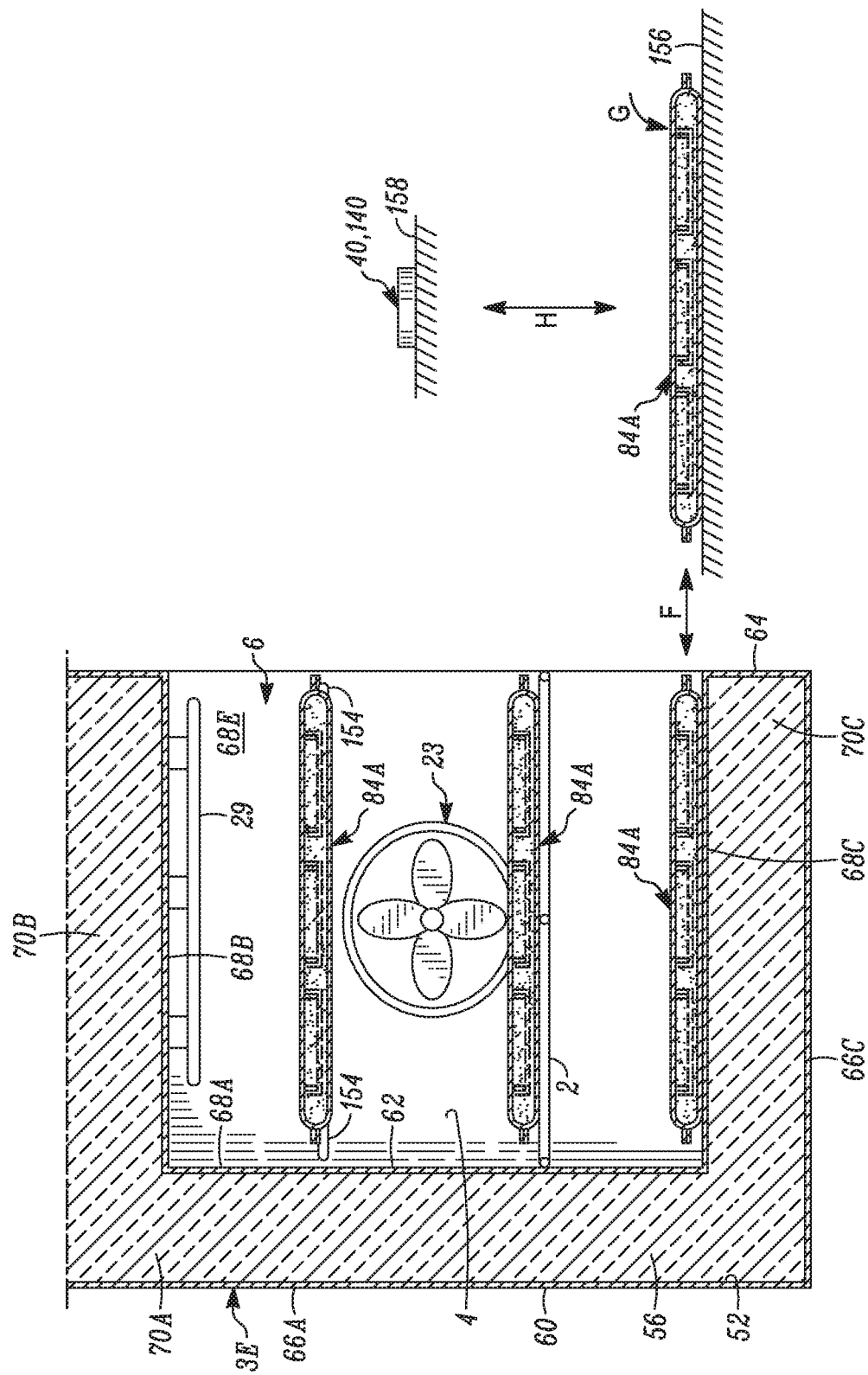
FIG. 16 is a sectional view similar to FIG. 15 with the door removed and portions cut away to illustrate the use of the PCM packets or shelves inside and outside of the chamber.

FIG. 16 illustrates an additional advantage of using packets or shelves 84A. More particularly, each shelf 84A is removable from and insertable into interior chamber 4 with items 40 thereon within recesses 128, as indicated at arrow F (block 161). Thus, a given packet 84A may be removed from interior chamber 4 and placed at a position outside the interior chamber 4 such as on a support surface 156 while the storage items 40, shown here as petri dishes 140, and the contents thereof, remain seated on the shelf within recesses 128 (block 163). While the storage items 40 and/or shelves 84A are removed from interior chamber 4, various procedures may be undertaken with regard to the storage items, either while the storage items are on or removed from the given shelf 84A or a similar shelf (block 164). Support surface 156 may, for example, be in the form of a table, or a counter which is part of a fume hood whereby fumes from the petri dishes or other items under the hood may be exhausted. During the culturing of cells 152, it is necessary for the cells to be fed a suitable food, as indicated at arrow G. Thus, a worker may feed the cells 152 on medium 150 while the petri dish is seated within recesses 128 on packet 84A while the packet is on support surface 156 within a fume hood or the like. When the petri dishes are placed within recesses such as recesses 128, or remain seated atop a PCM packet like packet 84 in FIG. 6, the PCM of the corresponding packet helps to maintain the desired temperature of the item 40, including the medium 150 and cells 152 while they are outside the interior chamber 4 of insulated chamber 1H or the like. In addition, FIG. 16 illustrates that a given petri dish or other storage item 40 may be removed from the shelf or packet 84A when both are outside interior chamber 4 in order that the storage item 40 may be manipulated for other purposes. For example, storage item 40 may be removed from the packet (arrow H) and seated on another support surface 158. Support surface 158 also represents, for example, a scale on which item 40 may be weighed, or a microscope so that cells 152 or other components of item 40 may be viewed under the microscope. After a given item 40 has been manipulated on surface 158 or by any given tool as desired, it may be returned to the recess of packet 84 (arrow H) and other items 40 may similarly be removed and reinserted on packet 84. Once all procedures involving storage items 40 have been performed outside the insulated chamber, packet 84 with the various items 40 may be reinserted into interior chamber 4 (block 165).

Each of the chambers of the present invention may also be configured with two or more PCMs each of which has a different melting or freezing point. Thus, for example, one or more of layers 72A-E of chamber 1 (FIGS. 2-4) or layers 72A-F of chamber 1A (FIG. 5) may be formed of one PCM having a first melting or freezing phase change temperature while one or more of the other of said layers 72 may be formed of a PCM having a second melting or freezing phase change temperature which is different than the first melting or freezing temperature. Similarly, the layer 72G within one of packets 84 of chambers 1B or 1C (FIG. 7-8) may be formed of a PCM having the first melting or freezing temperature while another one of the layers 72G of the corresponding chamber 1B or 1C is formed of a PCM having the second melting or freezing temperature. Likewise, the layers 72A of chambers 1D or 1E (FIGS. 9-10) may have the first melting or freezing temperature while the respective layer 72B has the second melting or freezing temperature. Moreover, any one of the above noted PCM layers 72 may be formed of two or more different PCMs each having different melting temperatures. Whether these two or more PCMs are in separate layers or intermixed, the chamber thus provides the corresponding PCM for the respective first, second or third selected internal temperature of the interior chamber. In addition, the encapsulated pellets 104 of chambers 1F and 1G (FIGS. 11 and 13) may include two or more batches of pellets 104 such that the PCM 58 within one batch has a melting or freezing phase change temperature which is different than that of the other batch or batches. Configuring the chambers to have PCMs with differing melting or freezing temperatures may be useful, for example, in the pharmaceutical industry. In particular, drug manufacturers run stability tests on various medicines respectively at 30 degrees C. and 40 degrees C. (104 degrees F.). Thus, the chambers of the present invention may be configured with one PCM having a melting point of about 30 degrees C. and another PCM having a melting point of about 40 degrees C. to facilitate maintaining the temperature of interior chamber 4 at the corresponding temperature as desired by the user. The melting or freezing phase change temperatures of the two PCMs in the above example are both, for example, above 0 degrees C. and above the typical ambient temperature or typical room temperature of about 22 degrees C. or 23 degrees C. However, two or more PCMs used with a given insulated chamber of the present invention may also be configured to have melting or freezing phase change temperatures which are both below 0 degrees C., the ambient temperature or the room temperature noted above, or may also be configured such that the phase change temperature of one of the PCMs is above one of these reference temperatures and the other is below the corresponding reference temperature.

Thus, where the chamber utilizes two phase change materials each having different melting or freezing phase change temperatures, the chamber may be operated to either heat or cool the first phase change material with one of the heating or cooling devices carried by the chamber to melt or freeze the first phase change material at its melting or freezing temperature while also heating or cooling the interior chamber to that temperature and incubating, storing or maintaining a given item within the interior chamber at about this first melting or freezing temperature. Subsequently, the chamber may be similarly operated to heat or cool the second phase change material and the interior chamber at a second melting or freezing phase change temperature of the second phase change material such that it melts or freezes. Then, either the item that was incubated, stored or maintained at the first temperature may also be incubated, stored or maintained at the second temperature (block 166), or it may be removed and another item may be inserted into interior chamber 4 (block 167) and incubated, stored or maintained at or near the second temperature (block 168). It is noted that the processes illustrated in FIG. 17 do not necessarily occur in the order shown nor are the processes necessarily separate as might be suggested by the arrows.

According to one embodiment, the phase change material 58 in FIG. 2 comprises a plurality of packets enclosing PCM material. An exemplary packet 84 is illustrated in FIG. 6.

Typically, each packet comprises a sealed container about 8"×12"×¼" thick. Thus, as illustrated in in the close-up view of FIG. 18, a gap 200 between an insulation layer 70A and the skin inner layer 62 is typically sized to accommodate a thickness of only one packet 84. The heating element 29A is also disposed within the gap 200 and in contact with the packet 84. In one embodiment this arrangement is repeated throughout the wall surfaces of the chamber.

Figure 19:
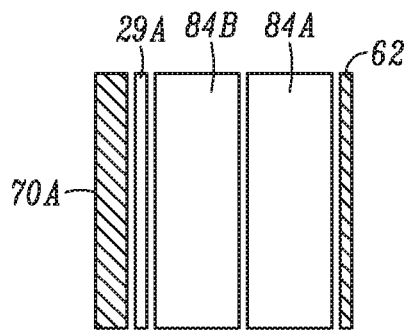

Of course, in another embodiment the gap 200 can be increased to accommodate two (or more) packets 84 oriented face-to-face as illustrated in FIG. 19, although such an embodiment may not be functionally advantageous.

Figure 20:
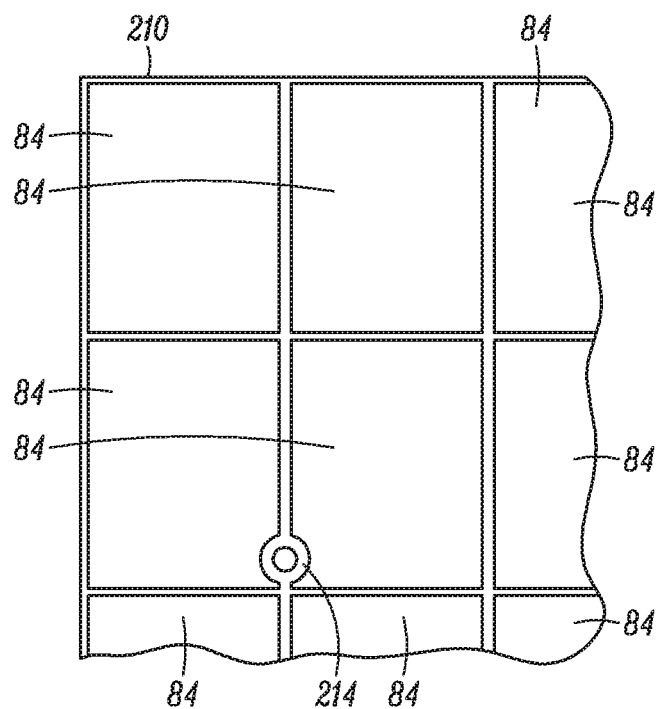
FIG. 20 is a sectional view through FIG. 18 illustrating PCM packets.

FIG. 20 illustrates a partial side view of a wall surface 210 of an incubation chamber, such as the back wall 42 of FIG. 2. A plurality of packets 84 are required to completely cover the wall surface 210 when the PCM packets 84 are oriented edge-to-edge. Since each PCM packet is about 8"×12" (in one embodiment) several rows and columns of packets are required to cover a wall surface of an incubation chamber that measures about 29 inches by 32 inches. This embodiment differs from that illustrated in FIG. 2 where the PCM 58 appears to be in the form of a continuous sheet or a continuous layer.

With the PCM in the form of packets (such as the packet 84) the packets can be arranged to create a small non-coverage area, i.e., voids between two adjacent packets. Wires and tubing, for example, can pass through chamber walls and through the voids between PCM packets. If the PCM was formed as a continuous layer or sheet this would not be possible as it would be necessary to seal edges of the PCM to create these openings for wires and tubing. With reference to FIG. 20, such an opening is designated by a reference numeral 214. The opening can be formed between two packets by simply slightly distorting two adjacent packets to create an opening between the two packets.

Figure 21:
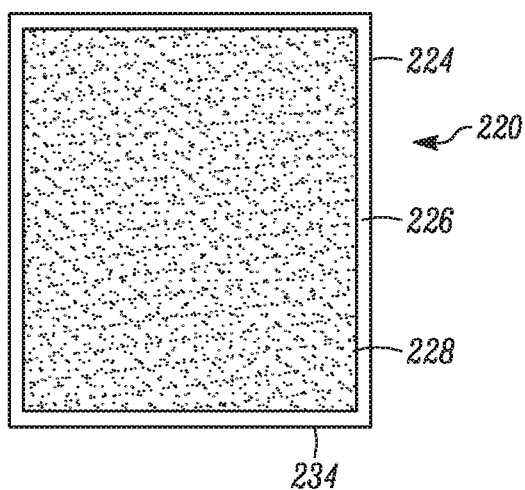
FIG. 21 is an illustration of a PCM packet.

In one embodiment, a foam sponge/wick is enclosed within each packet to absorb the PCM when in the liquid phase. This component supports a consistent vertical distribution of PCM while in the liquid phase, as gravity would otherwise cause the liquid PCM to pool at the lowest point of the packet. Such an embodiment is illustrated in a cutaway end view of FIG. 21, where each packet 220 comprises an exterior skin 224, a foam sponge/wick 226 within the packet and PCM 228.

The PCM permeates throughout the sponge/wick 226 as it absorbs the liquid-phase PCM. Since the PCM is distributed throughout the sponge/wick, when it transforms to a solid phase, the shape of the wick/sponge is retained while the PCM "freezes" in place. The sponge/wick thus allows the PCM to retain its geometric shape, i.e., the shape of the PCM packet does not significantly change as the PCM transitions from solid to liquid or vice versa.

Figure 18:
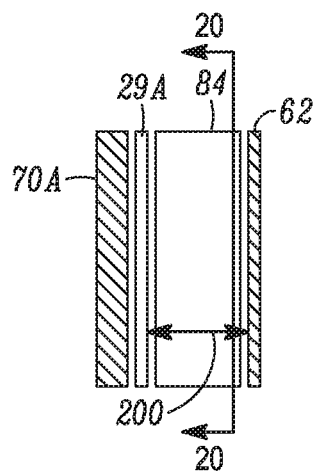
FIGS. 18 and 19 illustrate PCM packets between wall surfaces of the incubation chamber.

The foam sponge/wick 226 is flexible when the PCM is in the liquid phase. This allows local conformity to the gap 200 as illustrated in FIG. 18 and also the heating element 29A (one form of a temperature altering device) illustrated in FIG. 9. Conformity is important to maintain good thermal conductivity between the heating element and the PCM packet and the PCM to the inner skin 62.

When the PCM melts it expands thermally. The PCM packet must accommodate the additional volume required to contain the liquid PCM, while confining the PCM to a sealed container or within a sealed exterior skin. The PCM packets 220 are therefore sealed under a vacuum while creating extra volume to permit expansion.

In the embodiment described immediately above the PCM packets (FIG. 21) are disposed within one of more of the six surfaces of an incubation chamber as illustrated in exemplary FIGS. 18 and 20. In another embodiment the PCM is disposed within a rigid PCM container disposed within the incubation chamber.

In FIG. 7 the PCM container 84 is disposed beneath shelves 2 or on the top inner layer 68C of the bottom wall of the container 3; in FIG. 8 a PCM container 84 is horizontally disposed atop the tray 98 and a PCM container 84 is vertically disposed along the wall 88; in FIG. 15 the PCM is housed within a container that also serves as a shelf to store product. If a skin material of the container comprises a metal, the metal container provides a high thermal conductivity to items that are disposed atop the container and to the atmosphere within the chamber. In one embodiment the skin comprises a copper material, which provides the desired high thermal conductivity and also antimicrobial properties to minimize contamination at the microscopic level.

Returning to FIG. 15, a lowest container or shelf 84A is removably disposed atop the inner layer 68 C, and the containers 84A set atop a supporting surface or shelf whereby each packet 84A serves as a shelf on which the various items 40 are seated within interior chamber 4. It is advantageous to locate the PCM containers on a shelf or forming the shelf, as the PCM takes up less incubator space, leaving more space for the items 40.

Figure 24:
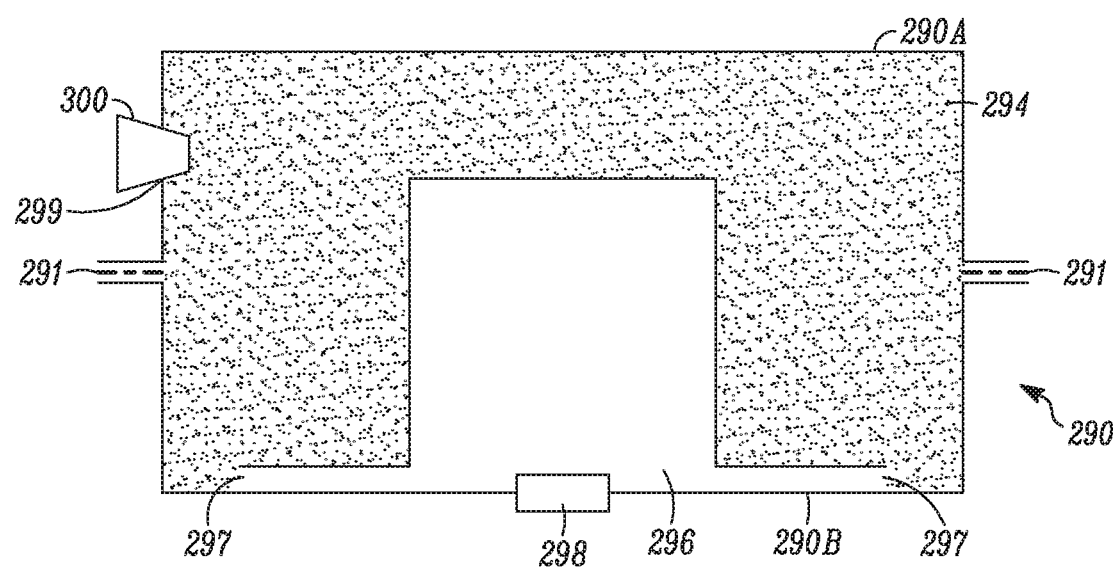
FIG. 24 is an illustration of a PCM container.

A PCM container 290 is illustrated in FIG. 24. The container 290 comprises a top section 290A and a bottom section 290B bonded with a liquid tight chemical adhesive bond 291. A material of the container comprises a rigid material with a relatively high thermal conductivity, such as a metallic material.

PCM 294 is disposed within the container 290. A flexible bladder 296 also within the container allows for thermal expansion of the PCM. The bladder is chemically bonded to the bottom surface 290B at lap joints 297. A top surface of the bladder 296 touches a bottom surface of the PCM 294 as illustrated.

The container further comprises an air vent 298 to relieve pressure created within the bladder by the expansion of the PCM as it melts and the resultant compression of the bladder.

The container also includes a fill port 299 and plug 300 for closing the fill port. PCM is loaded into the container cavity through the fill port 299.

In the embodiment illustrated in FIG. 24, the chamber contents (the end user's product) would be disposed atop the top section 290A of the container 290. Hot air rises by convection, and when the PCM is 'giving back heat' as it melts (for example, after electrical power has been lost due to a power failure or while transporting the chamber), it is preferable for the PCM to be physically located below the product to provide a convective heat transfer path to the product.

With the product in physical contact with the top section 290A, heat from the PCM (the heat source) also flows to the product by conduction. In this configuration the PCM container can also serve as a shelf. Since the top section 290A is in direct contact with the product, it is preferable to have the PCM disposed in contact with an inwardly-facing surface of the top section 290A, as this arrangement provides the shortest thermal transfer path from the PCM to the product Again, with the product in physical contact with the top section 290A but the PCM resting on the bottom section 290B, the heat transfer path begins at the PCM continues through the bottom section 290B, through the chemical adhesive bond 291 (which is an insulator), to the top section 290A, and finally reaching the product. Another heat transfer path with the PCM in contact with the bottom section 290B extends from the PCM to the bladder 296, into an air pocket (an insulator) that would be above the PCM, to the top section 290A and finally to the product. Both of these heat transfer paths are considerably longer than the path with the PCM in direct contact with the top section 290A and therefore not desired.

Typically, each of the bottom and top sections 290A and 290B comprise several plys or layers of material sheets that are bonded using a chemical adhesive, for example, a two-part epoxy. This technique prevents the liquid PCM from leaking from the container but avoids the use of mechanical fasteners and gaskets.

In a preferred embodiment, a first heater is disposed within the chamber walls (as described herein) and a second heater is disposed within the chamber interior. Typically, several minutes (hours) are required for the heater within the chamber walls to melt the PCM, also disposed within the walls in certain embodiments, and then warm the chamber interior. In certain applications this time interval may be too long. Thus for those applications the second heater (also referred to as an air heater or a boost heater) is placed in the chamber interior. The air heater raises the air temperature to about 37 degrees C. in a few minutes, while the heater within the chamber walls is warming the PCM. The air heater also aids in temperature recovery to 37 degrees C. after the chamber door has been opened as it heats the chamber air directly.

Various embodiments of the present invention include different door configurations, some of which are depicted in figures and described above. According to one embodiment the chamber comprises a solid door (i.e., no transparent glass) with PCM disposed therein. See FIG. 12 where PCM pellets 104 are disposed within the door 5B. Other forms of PCM may be used in the door in lieu of the pellets.

Figure 22:
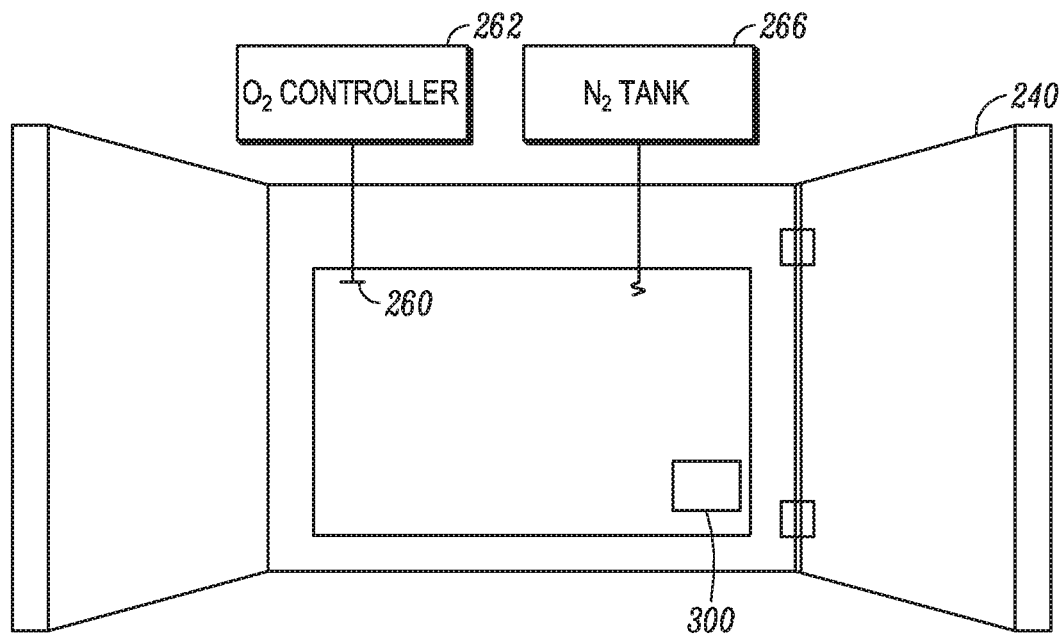
FIG. 22 is an illustration of an embodiment of an incubation chamber.

In another embodiment illustrated in FIG. 22 (omitting chamber interior details), access to the chamber interior is gained through two solid side-by-side doors 240, each having PCM disposed therein (not shown in FIG. 22). Opening either door provides access to the chamber interior. Either or both of the two doors may be constructed with or without a transparent glass front surface.

Figure 23:
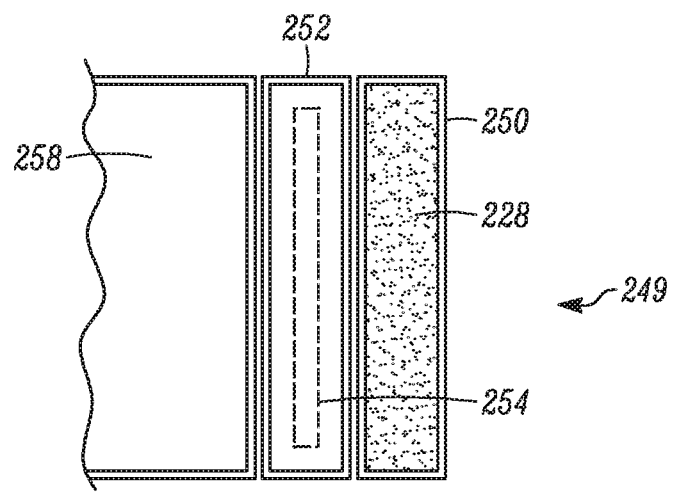
FIG. 23 is an illustration of a door arrangement of one embodiment of an incubation chamber.

In yet another embodiment (see the side view of FIG. 23) a chamber 249 comprises two doors in a parallel configuration, that is, both doors must be opened to gain access to a chamber interior region 258. With reference to FIG. 23, a solid (i.e., not having a transparent surface) outer door 250 contains PCM 228 therein. An inner door 252 includes a transparent viewing window 254. This configuration allows a user to view product in the chamber interior 258 by opening the outer door 250 and looking through the transparent viewing window 254, without disturbing the environment of the chamber interior 258. Clearly, both doors 250 and 252 must be opened to allow access to the interior region 258 and any product or specimens stored therein.

In one embodiment, an incubator chamber contains and an oxygen sensor 260 (see FIG. 22) and a controller 264. Oxygen depletion is accomplished by adding nitrogen to the chamber in a purge fashion from a nitrogen tank 266. In certain applications it is desired to maintain the oxygen within the chamber at a concentration below the ambient concentration of about 21% (e.g., a concentration of about 5% for growing human structural mammalian cells). Whenever the chamber door(s) are opened, the chamber interior air mixes with the ambient air, resulting in a chamber concentration of about 21%. To create an oxygen-deprived chamber environment the oxygen level is measured by the oxygen sensor 260 and nitrogen injected into the chamber from the nitrogen tank 266. The nitrogen ($N_2$) displaces the air mixture within the chamber in a purge type fashion, thus lowering the remaining oxygen ($O_2$), as well as argon, water vapor, and other elements within the chamber air.

The incubation chamber may contain a sterilization module 300 (see FIG. 22) as described in co-owned patent application filed on Dec. 19, 2016, assigned application Ser. No. 15/382,915 and entitled System and Method for Vaporized Hydrogen Peroxide Cleaning of an Incubation Chamber.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention is an example and the invention is not limited to the exact details shown or described.

What is claimed is:
1. An apparatus comprising:
 a closed container bounded by a plurality of surfaces defining a storage interior chamber adapted to receive therein a storage item;
 an insulation material layer disposed within an interior region of a first surface of the plurality of surfaces;
 a plurality of packets each containing first phase change material in a deformable packet enclosure, the plurality of packets disposed in the interior region and configured as a two dimensional array of detached packets, the array comprising a plurality of rows of separated packets and a plurality of columns of separated packets, wherein two side-by-side packets in the array of packets are deformed to create an opening therebetween for tubing or wires to pass through the opening, the first phase change material having a first melting or freezing phase change temperature; and
 a temperature-altering device disposed in the interior region and having a sheet-like shape, the temperature-altering device proximate the array of packets to control a temperature of the first phase change material.
2. The apparatus of claim 1 the temperature-altering device disposed in contact with the plurality of packets.
3. The apparatus of claim 1 wherein the temperature of the first phase change material also affects the temperature of the storage interior chamber.

4. The apparatus of claim 1 wherein each one of the plurality of packets is approximately 8 inches by 12 inches by ¼ inch thick.

5. The apparatus of claim 1 wherein the array of packets comprises a single layer of packets disposed within a gap defined between a material layer forming one of the plurality of surfaces and the insulation material layer.

6. The apparatus of claim 1 further comprising a wicking material disposed within one or more of the plurality of packets.

7. The apparatus of claim 1 further comprising a cooling device within the storage interior chamber.

8. The apparatus of claim 1 wherein the plurality of surfaces comprises a base, four upstanding sidewalls extending from the base, and a top, one of the upstanding sidewalls further comprising a door for providing access to the storage interior region when in an open configuration.

9. The apparatus of claim 8 the door comprising a side-by-side double door, each double door having phase change material disposed therein.

10. The apparatus of claim 8 the door comprising parallel-oriented inner and outer doors, the outer door having phase change material disposed therein and the inner door comprising a transparent region for viewing into the storage interior chamber, when the outer door is opened.

11. The apparatus of claim 1 wherein the first phase change material comprises phase change material pellets disposed within a liquid medium or within a solid matrix structure.

12. The apparatus of claim 1 further comprising a fan in fluid communication with the storage interior chamber, a humidity sensor and a humidity control unit for controlling humidity within the storage interior chamber, a carbon dioxide sensor and a carbon dioxide control unit for controlling a carbon dioxide level within the storage interior chamber, and an oxygen sensor and an oxygen control unit for controlling an oxygen level in the storage interior chamber.

13. The apparatus of claim 1 further comprising a sterilization module disposed within the storage interior chamber.

14. The apparatus of claim 1 further comprising a humidity control unit for controlling humidity within the storage interior chamber.

15. The apparatus of claim 1 the temperature-altering device comprising a first heating device and the apparatus further comprising a second heating device disposed in the storage interior chamber, the first heating device providing a heating-effect primarily by conduction and the second heating device providing a heating-effect primarily by convection.

16. The apparatus of claim 1 for at least one of the plurality of surfaces, beginning at the storage interior region the layers comprising, in order, an interior surface material layer, the plurality of packets, the temperature-altering device, the insulation material layer, and an exterior surface material layer.

17. The apparatus of claim 1 wherein the plurality of surfaces comprises five surfaces and a door, and wherein the plurality of packets is present in at least one of the five surfaces.

18. A first plurality of packets disposed in a first surface of the plurality of surfaces as in claim 1, the apparatus further comprising a second packet disposed within the storage interior chamber.

19. The apparatus of claim 18 the second packet disposed in a container forming a shelf within the storage interior chamber, the storage item disposed on the shelf such that heat transfer between the second packet and the storage item is by conduction.

20. The apparatus of claim 1 further comprising a removable shelf within the storage interior chamber, the shelf comprising a second phase change material and the storage item in contact with the removable shelf.

21. The apparatus of claim 1 comprising a removable container disposed within the storage interior chamber, the removable container further comprising a metal skin bounding a container interior chamber, a second phase change material disposed in the container interior chamber in contact with the metal skin, and the storage item disposed in contact with the metal skin.

22. The apparatus of claim 21 further comprising an outer surface of the removable container defining a recess therein, the storage item disposed within the recess.

23. The apparatus of claim 21 the metal skin comprising copper.

24. The apparatus of claim 21 further comprising a flexible bladder disposed within the container interior chamber, the container further comprising an air vent for relieving pressure created during expansion of the second phase change material.

25. The apparatus of claim 1 wherein the first phase change material has a melting temperature of 37 degrees C.

* * * * *